US007964579B2

(12) United States Patent
Mehta et al.

(10) Patent No.: US 7,964,579 B2
(45) Date of Patent: Jun. 21, 2011

(54) COMPOSITIONS AND METHODS FOR TOPICAL DELIVERY OF OLIGONUCLEOTIDES

(75) Inventors: Rahul C. Mehta, San Marco, CA (US); Gregory E. Hardee, Rancho Santa Fe, CA (US); Phillip Dan Cook, Fallbrook, CA (US); David J. Ecker, Encinitas, CA (US); Yali Jennifer Tsai, La Jolla, CA (US); Michael V. Templin, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 12/545,778

(22) Filed: Aug. 21, 2009

(65) Prior Publication Data

US 2009/0326045 A1 Dec. 31, 2009

Related U.S. Application Data

(63) Continuation of application No. 10/876,962, filed on Jun. 25, 2004, now abandoned, which is a continuation of application No. 09/315,294, filed on May 20, 1999, now Pat. No. 6,841,539, which is a continuation-in-part of application No. 09/082,336, filed on May 21, 1998, now abandoned.

(51) Int. Cl.
*C07H 21/02* (2006.01)
*C07H 21/04* (2006.01)
*A61K 31/70* (2006.01)
*C12Q 1/68* (2006.01)

(52) U.S. Cl. ............. 514/44 A; 536/23.1; 536/24.1; 536/24.5

(58) Field of Classification Search .............. None
See application file for complete search history.

(56) References Cited

U.S. PATENT DOCUMENTS

| | | |
|---|---|---|
| 3,687,808 A | 8/1972 | Merigan et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,689,320 A | 8/1987 | Kaji |
| 4,762,779 A | 8/1988 | Snitman |
| 4,789,737 A | 12/1988 | Miyoshi et al. |
| 4,806,463 A | 2/1989 | Goodchild et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yammane et al. |
| 4,904,582 A | 2/1990 | Tullis |
| 4,948,882 A | 8/1990 | Ruth |
| 4,958,013 A | 9/1990 | Letsinger |
| 4,981,957 A | 1/1991 | Lebleu et al. |
| 5,004,810 A | 4/1991 | Draper |
| 5,013,830 A | 5/1991 | Ohtsuka et al. |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,800 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,143,940 A | 9/1992 | Nurnberg et al. |
| 5,149,797 A | 9/1992 | Pederson et al. |
| 5,166,195 A | 11/1992 | Ecker |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,428 A | 3/1993 | Agrawal et al. |
| 5,212,295 A | 5/1993 | Cook |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,223,618 A | 6/1993 | Cook et al. |
| 5,235,033 A | 8/1993 | Summerton et al. |
| 5,242,906 A | 9/1993 | Pagano et al. |
| 5,245,022 A | 9/1993 | Weis et al. |
| 5,248,670 A | 9/1993 | Draper et al. |
| 5,254,469 A | 10/1993 | Warren, III et al. |
| 5,256,775 A | 10/1993 | Froehler |
| 5,258,506 A | 11/1993 | Urdea |

(Continued)

FOREIGN PATENT DOCUMENTS

WO  WO 93/24510  12/1993

(Continued)

OTHER PUBLICATIONS

U.S. Appl. No. 08/383,666, filed Feb. 3, 1995, Cook et al.
U.S. Appl. No. 08/465,880, filed Jun. 6, 1995, Cook.
U.S. Appl. No. 08/468,037, filed Jun. 5, 1995, Cook et al.
U.S. Appl. No. 08/762,588, filed Dec. 10, 1996, Cook et al.
U.S. Appl. No. 08/837,201, filed Apr. 14, 1997, Dean et al.
U.S. Appl. No. 08/910,629, filed Aug. 13, 1997, McKay et al.
U.S. Appl. No. 09/009,490, filed Jan. 20, 1998, Bennett et al.
U.S. Appl. No. 09/016,520, filed Jan. 30, 1998, Cook et al.
U.S. Appl. No. 09/044,506, filed Mar. 19, 1998, Bennett et al.
U.S. Appl. No. 09/062,416, filed Apr. 17, 1998, Bennett et al.

(Continued)

*Primary Examiner* — Sean R McGarry
(74) *Attorney, Agent, or Firm* — Knobbe Martens Olson & Bear—Irvine Office

(57) ABSTRACT

The present invention relates to compositions and methods which enhance the delivery of oligonucleotides and other nucleosidic moieties via topical routes of administration. Preferred compositions include liposomes or penetration enhancers for the delivery of such moieties to dermal and/or epidermal tissue in an animal for investigative, therapeutic or prophylactic purposes.

43 Claims, 2 Drawing Sheets

U.S. PATENT DOCUMENTS

| | | |
|---|---|---|
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,328,628 A | 7/1994 | Hart et al. |
| 5,338,837 A | 8/1994 | Kahne |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush et al. |
| 5,378,825 A | 1/1995 | Cook et al. |
| 5,386,023 A | 1/1995 | Sanghvi et al. |
| 5,391,723 A | 2/1995 | Priest |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,442,049 A | 8/1995 | Anderson et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,455,335 A | 10/1995 | Kahne et al. |
| 5,457,187 A | 10/1995 | Gmeiner et al. |
| 5,457,189 A | 10/1995 | Crooke et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,506,351 A | 4/1996 | McGee |
| 5,508,270 A | 4/1996 | Baxter et al. |
| 5,510,475 A | 4/1996 | Agrawal et al. |
| 5,512,439 A | 4/1996 | Hornes et al. |
| 5,512,667 A | 4/1996 | Reed et al. |
| 5,514,577 A | 5/1996 | Draper et al. |
| 5,514,785 A | 5/1996 | Van Ness et al. |
| 5,514,788 A | 5/1996 | Bennett et al. |
| 5,519,126 A | 5/1996 | Hecht |
| 5,519,134 A | 5/1996 | Acevedo et al. |
| 5,521,302 A | 5/1996 | Cook |
| 5,523,389 A | 6/1996 | Ecker et al. |
| 5,525,465 A | 6/1996 | Haralambidis et al. |
| 5,525,711 A | 6/1996 | Hawkins et al. |
| 5,534,496 A | 7/1996 | Lee et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,543,508 A | 8/1996 | Haseloff et al. |
| 5,545,729 A | 8/1996 | Goodchild et al. |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis et al. |
| 5,554,746 A | 9/1996 | Ravikumar et al. |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,571,902 A | 11/1996 | Ravikumar et al. |
| 5,574,142 A | 11/1996 | Meyer, Jr. et al. |
| 5,576,208 A | 11/1996 | Monia et al. |
| 5,576,427 A | 11/1996 | Cook et al. |
| 5,578,717 A | 11/1996 | Urdea et al. |
| 5,578,718 A | 11/1996 | Cook et al. |
| 5,580,575 A | 12/1996 | Unger et al. |
| 5,580,731 A | 12/1996 | Chang et al. |
| 5,580,767 A | 12/1996 | Cowsert et al. |
| 5,582,972 A | 12/1996 | Lima et al. |
| 5,582,986 A | 12/1996 | Monia et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,587,470 A | 12/1996 | Cook et al. |
| 5,591,584 A | 1/1997 | Chang et al. |
| 5,591,600 A | 1/1997 | Ecker |
| 5,591,623 A | 1/1997 | Bennett et al. |
| 5,591,720 A | 1/1997 | Anderson et al. |
| 5,591,722 A | 1/1997 | Montgomery et al. |
| 5,594,121 A | 1/1997 | Froehler et al. |
| 5,595,726 A | 1/1997 | Magda et al. |
| 5,595,978 A | 1/1997 | Draper et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,797 A | 2/1997 | Cook et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,607,923 A | 3/1997 | Cook et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,620,963 A | 4/1997 | Cook et al. |
| 5,622,712 A | 4/1997 | Eppstein et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,825 A | 7/1997 | Hillebrand et al. |
| 5,646,265 A | 7/1997 | McGee |
| 5,652,355 A | 7/1997 | Metelev et al. |
| 5,652,356 A | 7/1997 | Agrawal |
| 5,658,873 A | 8/1997 | Bertsch-Frank et al. |
| 5,658,891 A | 8/1997 | Draper et al. |
| 5,661,134 A | 8/1997 | Cook et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,747 A | 10/1997 | Boggs et al. |
| 5,681,941 A | 10/1997 | Cook et al. |
| 5,681,944 A | 10/1997 | Crooke et al. |
| 5,688,941 A | 11/1997 | Cook et al. |
| 5,691,461 A | 11/1997 | Ecker et al. |
| 5,697,248 A | 12/1997 | Brown |
| 5,700,920 A | 12/1997 | Altmann et al. |
| 5,700,922 A | 12/1997 | Cook |
| 5,705,188 A | 1/1998 | Junichi et al. |
| 5,707,648 A | 1/1998 | Yiv |
| 5,714,331 A | 2/1998 | Buchardt et al. |
| 5,716,780 A | 2/1998 | Edwards et al. |
| 5,719,262 A | 2/1998 | Buchardt et al. |
| 5,770,222 A | 6/1998 | Unger et al. |
| 5,801,154 A | 9/1998 | Baracchini et al. |
| 5,869,462 A | 2/1999 | Dzau |
| 5,877,309 A | 3/1999 | McKay et al. |

| | | |
|---|---|---|
| 5,906,822 A | 5/1999 | Samour et al. |
| 5,914,126 A | 6/1999 | Li et al. |
| 5,922,686 A | 7/1999 | Bennett et al. |
| 5,955,059 A | 9/1999 | Gilchrest et al. |
| 6,031,005 A | 2/2000 | Easterling |
| 6,111,094 A | 8/2000 | Bennett et al. |
| 6,582,908 B2 | 6/2003 | Fodor et al. |
| 2001/0053519 A1 | 12/2001 | Fodor et al. |
| 2003/0228597 A1 | 12/2003 | Cowsert et al. |

FOREIGN PATENT DOCUMENTS

| | | |
|---|---|---|
| WO | WO 94/02499 | 2/1994 |
| WO | WO 94/08003 | 4/1994 |
| WO | WO 94/16736 | 8/1994 |
| WO | WO 94/17093 | 8/1994 |
| WO | WO 94/18835 | 9/1994 |
| WO | WO 97/30731 | 8/1997 |
| WO | WO 97/38728 | 10/1997 |
| WO | WO 98/51278 | 11/1998 |
| WO | WO 99/01579 | 1/1999 |

OTHER PUBLICATIONS

Agrawal et al., "Pharmacokinetics of oligonucleotides" Civa Found Syrup (1997) 209:60-75.

Albert et al., "Antisense knockouts: molecular scalpels for the dissection of signal transduction" Trends. Pharmacol. Sci. (1994) 15:250-254.

Baker et al., "Cleavage of the 5' Cap Structure of mRNA by a Europium(III) Macrocyclic Complex and Pendant Alcohol Groups" J. Am. Chem. Soc. (1997) 119(38):8749-8755.

Berge et al., "Pharmaceutical Salts" J. Pharm. Sci. (1977) 66:1-19.

Berkow et al., "The Merck Manual of Diagnosis and Therapy" 15th Ed., Rahway, N.J. (1987) 2263-2277.

Berkow et al., "The Merck Manual of Diagnosis and Therapy" 15th Ed., Rahway, N.J. (1987) 2283-2285.

Berkow et al., "The Merck Manual of Diagnosis and Therapy" 15th Ed., Rahway, N.J. (1987) 2286-2292.

Berkow et al., "The Merck Manual of Diagnosis and Therapy" 15th Ed., Rahway, N.J. (1987) 2301-2310.

Bernhard et al., "Direct Evidence Linking Expression of Matrix Metalloproteinase 9 (92-kDA gelatinase/collagenase) to the metastatic phenotype in transformed rat embryo cells" PNAS (1994) 91:4293-4297.

Birkedal-Hansen, "Proteolytic Remodeling of Extracellular Matrix" Curr. Opin. Cell Biol. (1995) 7:728-735.

Block, "Emulsions and Microemulsions" in Pharmaceutical Dosage Forms, Lieberman et al. (1989) 2(9):335-378.

Boggemeyer et al., "Borrelia Burgdorferi Upregulates the Adhesion Molecule E-selectin, P-selectin, ICAM-1 and VCAM-1 on Mouse Endothelioma Cells in vitro" Cell Adhes. Commun. (1994) 2:145-157.

Branch, "A good antisense molecule is hard to find" TIBS (1998) 23:45-50.

Brand et al., "Iontophorectic delivery of a telomeric oligonucleotide" Pharmaceutical Research (1996) 13(6):851-854.

Brunton, "Agents Affecting Gastrointestinal Water Flux and motility: Emesis and Antiemetics; Bile Acids and Pancreatic Enzymes" Goodman & Gilman's The Pharmacological Basis of Therapeutics, 9th Ed., Hardman et al., McGraw-Hill, New York (1996) Chapter 38:934-735.

Buur et al., "Penetration of 5-Fluorouracil and prodrugs across the intestine of the albino rabbit: Evidence for shift in absorption site from the upper to the lower region of the gastrointestinal tract by prodrugs" J. Controlled Release (1990) 14:43-51.

Buzayan et al., "Satellite tobacco ringspot virus RNA: A subset of the RNA sequence is sufficient for autolytic processing" PNAS (1986) 83:8859-8862.

Chiang et al., "Antisense Oligonucleotides Inhibit Intercellular Adhesion Molecule 1 Expression by Two Distinct Mechanisms" J. Biol. Chem. (1991) 266:18162-18171.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Choi et al., "Control of scarring in adult wounds using antisense transforming growth factor-B1 oligodeoxynucleotides" Immunology and Cell Biology (1976) 74:144-150.

Clarenc et al., "Delivery of antisense oligonucleotides by poly(L-lysine)conjugation and liposome encapsulation" Anti-Cancer Drug Design (1993) 8:89-91.

Cole-Strauss et al., "Correction of the Mutation Responsible for Sickle Cell Anemia by an RNA-DNA Oligonucleotide" Science (1996) 273:1386-1389.

Constantinides et al., "Formulation and Intestinal Absorption Enhancement Evaluation of Water-in-Oil Microemulsions Incorporating Medium-Chain Glycerides" Pharm. Res. (1994) 11:1385-1390.

Crooke et al., "Pharmacokinetic Properties of Several Novel Oligonucleotide Analogs in mice" J. Pharmacol. Exp. Therapeutics (1996) 277:923-937.

Crooke, "Progress in Antisense Therapeutics" Hematologic Path. (1995) 9:59-72.

Crooke et al., "Progress in the development and patenting of antisense drug discovery technology" Exp. Opin. Ther. Patents (1996) 6:855-870.

Crooke et al., "Basic Principles of Antisense Therapeutics" Antisense Research and Application (1998) Chapter 1:1-50.

De Mesmaeker et al., "Antisense Oligonucleotides" Acc. Chem. Res. (1995) 28:366-374.

Dean et al., "Inhibition of protein kinase C-a expression in mice after systemic administration of phosphorthioate antisense oligodeoxynucleotides" PNAS (1994) 91:11762-11766.

Delisser et al., "Molecular and Functional Aspects of PECAM-1/CD31" Immunol. Today (1994) 15(10):490-494.

Downward, "The ras Superfamily of Small GTP-binding proteins" TIBS (1990) 15:469-472.

Du Plessis et al., "Topical Delivery of Liposomally Encapsulated Gamma-Interferon" Antiviral Res. (1992) 18:259-265.

El-Hariri et al., "The Mitigating Effects of Phosphatidylcholines on Bile Salt- and Lysophosphatidylcholine-induced Membrane Damage" J. Pharm. Pharmacol. (1992) 44:651-654.

Ellington et al., "In Vitro selection of RNA molecules that bind specific ligands" Nature (1990) 346:818-822.

Englisch et al., "Chemically Modified Oligonucleotides as Probes and Inhibitors" Angew. Chem. Int. Ed. Eng. (1991) 30:613-629.

Forster et al., "External Guide Sequences for an RNA Enzyme" Science (1990) 249:783-786.

Forster et al., "Self-Cleavage of Virusoid RNA is Performed by the Proposed 55-Nucleotide Active Site" Cell (1987) 50:9-16.

Freier et al., "The ups and downs of nucleic acid duplex stability: structure-stability studies on chemically-modified DNA:RNA duplexes" Nucl. Acids Res. (1997) 25:4429-4443.

Green et al., "Antisense Oligonucleotides: An Evolving Technology for the Modulation of Gene Expression in Human Disease" American College of Surgeons (2000) 93-105.

Griffiths et al., "Keratinocyte Intercellular Adhesion Molecule-1 (ICAM-1) Expression Preceedes Derman T Lymphocyte Infiltration in Allergic Contact Dermatitis (Rhus dermatitis)" Am. J. Pathology (1989) 135:1045-1053.

Guerrier-Takada et al., "Phenotypic Conversion of Drug-Resistant Bacteria to Drug Sensitivity" PNAS (1997) 94:8468-8472.

Gum et al., "Stimulation of 92-kDa Gelatinase B Promoter Activity by ras Is Mitogen-activated Protein Kinase Kinase 1-independent and Requires Multiple Transcription Factor Binding Sites Including Closely Spaced PEA3/ets and AP-1 Sequences" J. Biol. Chem. (1996) 271(18):10672-10680.

Hakugawa et al., "The Inhibitory Effect of Anti-Adhesion Molecule Antibodies on Eosinophil Infiltration in Cutaneous Late Phase Response in Balb/c Mice Sensitized with Ovalbumin (OVA)" J. Dermatol. (1997) 24:73-79.

Haseloff et al., "Simple RNA enzymes with new and highly specific endoribonuclease activities" Nature (1988) 334: 585-591.

Hegemann et al., "Biochemical Pharmacology of Protein Kinase C and its Relevance for Dermatology" Pharmcology of the Skin, Mukhtar, H. (eds.), CRC Press, Boca Raton (1992) 22:257-268.

Higuchi et al., "Particle Phenomena and Coarse Dispersions" in Reminton's Pharmaceutical Sciences, Mack Publishing Co., Easton, PA (1985) 21:301-329.

Himelstein et al., "Metalloproteinases in Tumor Progression: The Contribution of MMP-9" Invasion & Metastasis (1994-1995) 14:246-258.

Ho et al., "Treatment of severe lichen planus with cyclosporine" J. Am. Acad. Dermatol. (1990) 22:64-68.

Ho et al., "Preparation of Microemulsions Using Polyglycerol Fatty Acid Esters as Surfactant for the Delivery of Protein Drugs" J. Pharm. Sci. (1996) 85:138-143.

Hua et al., "Inhibition of Matrix Metalloproteinase 9 Expression by a Ribozyme Blocks Metastasis in a Rat Sarcoma Model System" Cancer Res. (1996) 56:5279-5284.

Hurtenbach et al., "Prednisolone Reduces Experimental Arthritis and Inflammatory Tissue Destruction in Scid Mice Infected with Borrelia Burgdorferi" Int. J. Immunopharmac. (1996) 18(5):281-288.

Hyrup et al., "Peptide Nucleic Acids (PNA): Synthesis, Properties, and Potential Applications" Biorg. & Med. Chem. (1996) 4:5-23.

Idson, "Pharmaceutical Emulsion" in Pharmaceutical Dosage Forms, Lieberman et al. (eds.) (1988) 1(6):199-243.

Jarrett et al., "Affinity chromatography with nucleic acid polymers" J. Chromatog. (1993) 618:315-339.

Jen et al., "Suppression of Gene Expression by Targeted Disruption of Messenger RNA: Available Options and Current Strategies" Stem Cells (2000) 18:307-319.

Kabanov, "A new class of antivirals: antisense oligonucleotides combined with a hydrophobic substituent effectively inhibit influenza virus reproduction and synthesis of virus-specific proteins in MDCK cells" FEBS Letts. (1990) 259:327-330.

Katocs et al., "Biological Testing" Remington's Pharmaceutical Sciences, 18th Ed. Gennaro (ed.) Mack Publishing Co., Easton, PA (1990) 27:484-494.

Herbert et al., "Protein Kinase C Alpha Expression Is Required for Heparin Inhibition of Rat Smooth Muscle Cell Proliferation in Vitro and In Vivo" The Journal of Biological Chemistry (1996) 271(42):25928-25935.

Herbert et al., "Intimal Hyperplasia Following Vascular Injury Is Not Inhibited by an Antisense Thrombin Receptor Oligodeoxynucleotide" Journal of Cellular Physiology (1997) 170:106-114.

Kerr et al., "TGF-B1 Inhibition of Transin/Stromelysin Gene Expression is Mediated Through a Fos Binding Sequence" Cell (1990) 61:267-278.

Kerr et al., "Growth Factors Regulate Transin Gene Expression by c-fos-Dependent and c-fos-Independent Pathways" Science (1988) 242:1424-1427.

Kroschwitz, "Polynucleotides" Concise Encyclopedia of Polymer Science and Engineering (1990) John Wiley & Sons, New York, 858-859.

Lee et al., "Mucosal Penetration Enhancers for Facilitation of Peptide and Protein Drug Absorption" Crit. Rev. Ther. Drug Carrier Systems (1991) 8:91-192.

Letsinger et al., "Cholesteryl-conjugated oligonucleotides: Synthesis, properties and activity as inhibitors of replication of human immunodeficiency virus in cell culture" PNAS (1989) 86:6553-6556.

Leung et al., "Microemulsions: An Evolving Technology for Pharmaceutical Applications" in Controlled Release of Drugs: Polymers and Aggregate Systems, Rosoff, M. (ed.) VCH Publishers, New York (1989) 6:185-215.

Lisby et al., "Intercellular adhesion molecule-1 (ICAM-1) expression correlated to inflammation" Br. J. Dermatol. (1989) 120:479-484.

Litwin et al., "Novel Cytokine-independent Induction of Endothelial Adhesion Molecules Regulated by Platelet/Endothelial Cell Adhesion Molecule (CD31)" J. Cell Biol. (1997) 139(1):219-228.

Manoharan et al., "Cholic Acid-Oligonucleotide Conjugates for Antisense Applications" Bioorganic Med. Chem. Letts. (1994) 4:1053-1060.

Manoharan et al., "Chemical Modifications to Improve Uptake and Bioavailability of Antisense Oligonucleotides" Annals NY Acad. Sciences (1992) 660:306-309.

Manoharan et al., "Introduction of a Lipophilic Thioether Tether in the Minor Groove of Nucleic Acids for Antisense Applications" Bioorg. Med. Chem. Letts. (1993) 3:2765-2770.

Manoharan et al., "Lipidic Nucleic Acids" Tetrahedron Letts. (1995) 36:3651-3654.

Martin, "Ein neuer Zugang zu 2'-O-Alkyribonucleosiden und Eigenschaften deren Oligonucleotide" Helvetica Chemica Acta (1995) 78:486-504 (English summary included).

McCullough et al., "Regulation of Epidermal Proliferation in Mouse Epidermis by Combination of Difluoromethyl Ornithine (DFMO) and Methylglyoxal Bis(guanylhdrazone) (MGBG)" J. Investigative Dermatology (1985) 85:518-521.

Mishra et al., "Improved leishmanicidal effect of phosphorotioate antisense oligonucleotides by LDL-medicated delivery" Biochem. Et Biophysica (1995) 1264:229-237.

Miyao et al., "Stability and Pharmacokinetic Characteristics of Oligonucleotides Modified at Terminal Linkages in Mice" Antisense Res. & Dev. (1995) 5:115-121.

Muranishi, "Absorption Enhancers" Crit. Rev. Ther. Drug Carrier Systems (1990) 7:1-33.

New England Biolabs 1998/99 Catalog (cover page and pp. 121 and 284).

Newman, "Perspective Series: Cell Adhesion in Vascular Biology" The Biology of PECAM-1, J. Clin. Invest. (1997) 99(1):3-7.

Nielsen et al., "Sequence-Selective Recognition of DNA by Strand Displacement with a Thymine-Substituted Polyamide" Science (1991) 254:1497-1500.

Niels et al., "Principles of Therapeutics" Goodman & Gilman's The Pharmacological Basis of Therapetuics, 9th Ed. Hardman et al. (eds.) McGraw-Hill, New York, NY (1996) 3:43-62.

Nolen III et al., "Percutaneous penetration of methyl phosphonate antisense oligonucleotides" Intl. J. Pharm. (1994) 107:169-177.

Oberhauser et al., "Effective incorporation of 2'-O-methyl-oligonucleotides into liposomes and enhanced cell association through modification with thiocholesterol" Nucl. Acids Res. (1992) 20:533-538.

Oldenburg et al., "Iontopheretic delivery of oligonucleotides across full thickness hairless mouse skin" Journal of Pharmaceutical Sciences (1995) 84(8):915-921.

Regezi et al., "Vascular Adhesion Molecules in Oral Lichen Planus" Oral Surg. Oral Med. Oral Pathol. (1996) 81:682-690.

Reynolds et al., "Rational siRNA design for RNA interference" Nature Biotechnology (2004) 22(3):326-330.

Rieger, "Surfactants" in Pharmaceutical Dosage Forms, Lieberman et al. (eds.) Marcel Dekker, Inc., New York, NY (1988) 1:285-366.

Ritschel, "Microemulsions for Improved Peptide Absorption from the Gastrointestinal Tract" Meth. Find. Exp. Clin. Pharmacol. (1991) 13(3):205-220.

Rosoff, "Specialized Pharmaceutical Emulsions" Pharmaceutical Dosage Forms—Disperse Systems H.A. Lieberman (eds.), Marcel Dekker, Inc., New York (1988) 1(7):245-283.

Ruoslahti, "How Cancer Spreads" Sci. Am. (1996) 72-77.

Saison-Behmoaras et al., "Short modified antisense oligonucleotides directed against Ha-ras point mutation induce selective cleavage of the mRNA and inhibit T24 cells proliferation" EMBO J. (1991) 10:1111-1118.

Sanghvi, "Heterocyclic Base Modifications in Nucleic acids and their Applications in Antisense Oligonucleotides" Antisense Research and Applications (1993) Chapter 15, CRC Press, Boca Raton, 273-288.

Schott, "Colloidal Dispersions" in Remington's Pharmaceutical Sciences, Mack Publishing Co., Easton, PA (1985) 20:271-300.

Shea et al., "Synthesis, hybridization properties and antiviral activity of lipid-oligodeoxynucleotide conjugates" Nucl. Acids Res. (1990) 18:3777-3783.

Shiohara et al., "Fixed drug Eruption: Expression of Epidermal Keratinocyte Intercellular Adhesion Molecule-1 (ICAM-1)" Arch. Dermatol. (1989) 125:1371-1376.

Smith, "Automated Synthesis and Sequence Analysis" Analyt. Chem. (1988) 60:381-390.

Stein et al., "Preparation of S-Labeled Polyphosphorothioate Oligodeoxyribonucleotides by Use of Hydrogen Phosphonate Chemistry" Anal. Biochem. (1990) 188:11-16.

Stepowski et al., "Blocking of Heart Allograft Rejection by Intercellular Adhesion Molecule-1 Antisense Oligonucleotides Alone or in Combinations with Other Immunorepressive Modalities" J. Immunology (1994) 153:5336-5346.

Stetler-Stevenson et al., "Tumor Cell Interactions with the Extracellular Matrix During Invasion and Metastasis" Annu. Rev. Cell Biol., Palade, G.E. et al. (eds.) (1993) 9:541-573.

Supplementary Partial European Search Report for EP Application No. 99923252.3 dated Jun. 27, 2003.

Supplementary European Search Report for EP Application No. 99923252.3 dated Mar. 4, 2004.

Svinarchuk et al., "Inhibition of HIV proliferation in MT-4 cells by antisense oligonucleotide conjugated to lipophilic groups" Biochimie (1993) 79:49-54.

Swinyard et al., "Gastrointestinal Drugs" Remington's Pharmaceutical Sciences, 18th Ed. Gennaro (ed.), Mack Publishing Co., Easton, PA (1990) Chapter 39:774, 782-783.

Takahashi et al., "The Use of a Perfluorochemical Emulsion as a Bascular Perfusate in Drug Absorption" J. Pharm. Pharmacol. (1988) 40:252-257.

Takakura et al., "Uptake Characteristics of Oligonucleotides in the Isolated Rat Liver Perfusion System" Antisense & Nuc. Acid Drug Dev. (1996) 6:177-183.

U.S. Congress, Office of Technology Assesment, "The State-of-the-art in Genetic Screening" Genetic Monitoring and Screening in the Workplace, OTA-BA-445, U.S. Government Printing Office, Washington, D.C. (1990) Chapter 5:77-99.

Van Berge-Henegouwen, "Pharmacology and Chenodeoxycholic Acid" Gastroenterology (1977) 73:300-309.

Wahlestedt et al., "Modulation of Anxiety and Neuropeptide Y-Y1 Receptors by Antisense Oligodeoxynucleotides" Science (1993) 259:528-531.

Wahlestedt et al., "Antisense oligodeoxynucleotides to NMDA-R1 receptor channel protect cortical neurons from excitotoxicity and reduce focal ischaemic infarctions" Nature (1993) 363:260-263.

Wang et al., "Plasmid DNA Absorbed to PH-Sensitive Liposomes Efficiently Transforms the Target Cells" Biochem. Biophys. Res. Commun. (1987) 147(3): 980-985.

Warren et al., "Protocols for Oligonucleotides Conjugates" Methods in Molecular Biology Agrawal (ed.) Humana Press, Totowa, NJ (1994) vol. 26, Chapter 9, 233-264.

Weiner et al., "Liposomes: A Novel Topical Delivery System for Pharmaceutical and Cosmetic Applications" J. Drug Targeting (1994) 2:405-410.

Yamamoto et al., "A Mechanistic study on Enhancement of Rectal Permeability to Insulin in the Albino Rabbit" J. Pharm. Exp. Ther. (1992) 263:25-31.

Yamashita et al., "Effects of diclofenac sodium and disodium ethylenediaminetetraacetate on electrical parameters of the mucosal membrane and their relation to the permeability enhancing effects in the rat jejunum" J. Pharm. Pharmacol. (1987) 39:621-626.

Yamashita et al., "Effects of Adjubants on charge-Selective Permeability and Electrical Resistance on Rat Jejunal Membrane" J. Pharm. Sci. (1990) 79:579-583.

Zhou et al., "Targeted Delivery of DNA by Liposomes and Polymers" J. Controll. Release (1992) 19:269-274.

Zuker, "On Finding All Suboptimal Foldings of an RNA Molecule" Science (1989) 244:48-52.

Examiner's Report No. 2 for Australian Application No. 40069/99 dated Apr. 10, 2002.

Final Rejection for U.S. Appl. No. 09/082,336 dated Aug. 16, 2000.

Final Rejection for U.S. Appl. No. 09/315,294 dated Jul. 6, 2001.

Final Rejection for U.S. Appl. No. 10/876,962 dated Oct. 4, 2007.

Notice of Allowance for U.S. Appl. No. 09/315,294 dated Mar. 22, 2004.

Office Action for U.S. Appl. No. 09/082,336 dated Jul. 20, 1999.

Office Action for U.S. Appl. No. 09/082,336 dated Feb. 2, 2000.

Office Action for U.S. Appl. No. 09/082,336 dated Apr. 9, 2001.

Office Action for U.S. Appl. No. 09/315,294 dated Oct. 2, 2000.

Office Action for U.S. Appl. No. 09/315,294 dated Nov. 1, 2001.

Office Action for U.S. Appl. No. 09/315,294 dated Dec. 10, 2002.

Office Action for U.S. Appl. No. 09/315,294 dated Sep. 26, 2003.

Office Action for U.S. Appl. No. 10/876,962 dated Jan. 19, 2007.

Office Action for U.S. Appl. No. 10/876,962 dated Feb. 6, 2008.

Office Action for U.S. Appl. No. 10/876,962 dated Feb. 24, 2009.

Restriction Requirement for U.S. Appl. No. 09/315,294 dated Apr. 30, 2002.

International Search Report for PCT/US99/11142 dated Sep. 10, 1999.

| Skin Condition | n | Expt. Duration (hrs.) | Vehicle Enhancer | Animal Gender | Epidermal Penetration | | Dermal Penetration | | Receptor Penetration | |
|---|---|---|---|---|---|---|---|---|---|---|
| | | | | | AVG | S.E. | AVG | S.E. | AVG | S.E. |
| frozen | 4 | 24 | oleic acid | female | 1.24 | 0.08 | 0.99 | 0.21 | 0.04 | 0.01 |
| frozen | 4 | 24 | limonene | female | 1.55 | 0.17 | 0.72 | 0.09 | 0.09 | 0.00 |
| frozen | 5 | 24 | IPM | female | 1.67 | 0.27 | 0.13 | 0.03 | 0.06 | 0.01 |
| frozen | 3 | 24 | EtOH/ limonene | female | 1.89 | 0.08 | 0.86 | 0.04 | 0.03 | 0.05 |
| frozen | 3 | 24 | 30 µl limonene | female | 1.91 | 0.16 | 1.10 | 0.08 | 0.10 | 0.02 |
| frozen | 3 | 24 | 30 µl IPM | female | 3.21 | 0.23 | 1.32 | 0.15 | 0.10 | 0.06 |
| frozen | 4 | 24 | Tween 40 | female | 1.18 | 0.21 | 1.42 | 0.24 | 0.11 | 0.04 |
| frozen | 9 | 36 | buffer | male | 0.73 | 0.06 | 0.01 | 0.00 | 0.01 | 0.00 |
| fresh | 9 | 24 | buffer | male | 0.60 | 0.04 | 0.02 | 0.00 | 0.00 | 0.00 |
| fresh | 9 | 24 | PG 100% | male | 1.49 | 0.10 | 0.00 | 0.00 | 0.00 | 0.00 |
| frozen | 9 | 24 | IPM | male | 3.11 | 0.23 | 0.17 | 0.01 | 0.00 | 0.00 |
| fresh | 8 | 24 | 50% PG | male | 1.10 | 0.07 | 0.02 | 0.00 | 0.00 | 0.00 |
| fresh | 4 | 24 | 75% PG | male | 0.97 | 0.08 | 0.05 | 0.02 | 0.05 | 0.03 |
| fresh | 4 | 24 | 25% PG | male | 0.97 | 0.07 | 0.04 | 0.03 | 0.00 | 0.01 |
| frozen | 4 | 24 | IPM | male | 2.14 | 0.31 | 0.13 | 0.23 | 0.06 | 0.02 |
| frozen | 3 | 24 | Miglyol 818 | male | 1.62 | 0.11 | 0.09 | 0.04 | 0.02 | 0.01 |
| fresh | 4 | 24 | 1dodecyl2pyrrol | female | 0.27 | 0.05 | 0.67 | 0.25 | 0.04 | 0.02 |
| fresh | 4 | 24 | DMSO | female | 1.56 | 0.09 | 0.38 | 0.09 | 0.05 | 0.03 |
| fresh | 4 | 24 | 1Methyl 2pyrrol | female | 2.41 | 0.17 | 0.25 | 0.02 | 0.02 | 0.01 |
| fresh | 3 | 24 | ethylene glycol | female | 2.41 | 0.21 | 0.12 | 0.06 | 0.06 | 0.05 |
| fresh | 3 | 24 | menthone | female | 2.93 | 0.17 | 0.18 | 0.02 | 0.04 | 0.01 |
| fresh | 4 | 24 | azone | female | 1.31 | 0.18 | 0.16 | 0.03 | 0.01 | 0.01 |
| frozen | 3 | 24 | azone (no wash) | female | 0.73 | 0.07 | 0.13 | 0.05 | 0.02 | 0.00 |
| fresh | 3 | 24 | 10% SDS | female | 1.59 | 0.08 | 0.19 | 0.03 | 0.04 | 0.01 |
| fresh | 5 | 24 | terpinol | female | 1.11 | 0.08 | 0.14 | 0.01 | 0.06 | 0.05 |

Fig. 1

| Skin Condition | n | Expt. Duration (hrs.) | Vehicle Enhancer | Animal Gender | Epidermal Penetration | | Dermal Penetration | | Receptor Penetration | |
|---|---|---|---|---|---|---|---|---|---|---|
| | | | | | AVG | S.E. | AVG | S.E. | AVG | S.E. |
| frozen | 3 | 24 | 10% IPM | female | 0.56 | 0.12 | 0.12 | 0.02 | 0.01 | 0.00 |
| frozen | 3 | 24 | 35% IPM | female | 0.41 | 0.04 | 0.27 | 0.09 | 0.01 | 0.00 |
| frozen | 3 | 24 | 2mg IPM | female | 1.10 | 0.25 | 4.64 | 0.80 | 0.15 | 0.05 |
| frozen | 3 | 24 | 0.5mg IPM | female | 1.02 | 0.06 | 2.16 | 1.11 | 0.08 | 0.06 |
| frozen | 3 | 24 | 0.1mg IPM | female | 7.45 | 0.52 | 4.67 | 1.67 | 0.06 | 0.01 |
| frozen | 4 | 24 | 48% IPM Ceam | female | 1.56 | 0.22 | 1.70 | 0.31 | 0.00 | 0.00 |
| frozen | 3 | 24 | 30%IPM Cream | female | 1.66 | 0.28 | 1.57 | 0.40 | 0.00 | 0.00 |
| frozen | 7 | 24 | 15839/IPM | female | 1.46 | 0.13 | 2.40 | 0.24 | 0.00 | 0.00 |
| frozen | 4 | 24 | 15839/30% IPM Cream | female | 2.77 | 0.62 | 11.00 | 3.20 | 0.00 | 0.00 |
| fresh | 5 | 24 | IPM (2 hr) | female | 2.19 | 0.08 | 0.19 | 0.06 | 0.00 | 0.00 |
| fresh | 5 | 24 | IPM (3 hr) | female | 1.93 | 0.14 | 0.18 | 0.05 | 0.00 | 0.00 |
| fresh | 4 | 24 | IPM (30 min) | female | 2.15 | 0.36 | 0.11 | 0.04 | 0.01 | 0.00 |
| frozen | 4 | 24 | 2302/30% IPM Cream | female | 1.62 | 0.31 | 1.06 | 0.07 | 0.00 | 0.00 |

Fig. 2

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: antisense

<400> SEQUENCE: 1
gcccaagctg gcatccgtca                                                    20

<210> SEQ ID NO 2
<211> LENGTH: 20
<212> TYPE: DNA
<213> ORGANISM: Artificial Sequence
<220> FEATURE:
<223> OTHER INFORMATION: antisense

<400> SEQUENCE: 2
cccccaccac ttcccctctc                                                    20

<210> SEQ ID NO 3
<211> LENGTH: 20
<212> TYPE: DNA
<213> ORGANISM: Artificial Sequence
<220> FEATURE:
<223> OTHER INFORMATION: antiSense

<400> SEQUENCE: 3
```

-continued tgcatccccc aggccaccat                                           20

<210> SEQ ID NO 4
<211> LENGTH: 20
<212> TYPE: DNA
<213> ORGANISM: Artificial Sequence
<220> FEATURE:
<223> OTHER INFORMATION: antisense

<400> SEQUENCE: 4
tccgtcatcg ctcctcaggg                                           20

<210> SEQ ID NO 5
<211> LENGTH: 21
<212> TYPE: DNA
<213> ORGANISM: Artificial Sequence
<220> FEATURE:
<223> OTHER INFORMATION: antiSense

<400> SEQUENCE: 5
gcgtttgctc ttcttcttgc g                                         21

<210> SEQ ID NO 6
<211> LENGTH: 20
<212> TYPE: DNA
<213> ORGANISM: Artificial Sequence
<220> FEATURE:
<223> OTHER INFORMATION: antiSense

<400> SEQUENCE: 6
gttctcgctg gtgagtttca                                           20

<210> SEQ ID NO 7
<211> LENGTH: 15
<212> TYPE: DNA
<213> ORGANISM: Artificial Sequence
<220> FEATURE:
<223> OTHER INFORMATION: antiSense

<400> SEQUENCE: 7
aacttgtgct tgctc                                                15

<210> SEQ ID NO 8
<211> LENGTH: 20
<212> TYPE: DNA
<213> ORGANISM: Artificial Sequence
<220> FEATURE:
<223> OTHER INFORMATION: antiSense

<400> SEQUENCE: 8
tcccgcctgt gacatgcatt                                           20

<210> SEQ ID NO 9
<211> LENGTH: 20
<212> TYPE: DNA
<213> ORGANISM: Artificial Sequence
<220> FEATURE:
<223> OTHER INFORMATION: antiSense

<400> SEQUENCE: 9
gtgctcatgg tgcacggtct                                           20

<210> SEQ ID NO 10
<211> LENGTH: 20
<212> TYPE: DNA
<213> ORGANISM: Artificial Sequence
<220> FEATURE:

```
<223> OTHER INFORMATION: antisense

<400> SEQUENCE: 10
gtgtgccaga caccctatct                                              20

<210> SEQ ID NO 11
<211> LENGTH: 20
<212> TYPE: DNA
<213> ORGANISM: Artificial Sequence
<220> FEATURE:
<223> OTHER INFORMATION: antisense

<400> SEQUENCE: 11
gctgattaga gagaggtccc                                              20

<210> SEQ ID NO 12
<211> LENGTH: 20
<212> TYPE: DNA
<213> ORGANISM: Artificial Sequence
<220> FEATURE:
<223> OTHER INFORMATION: antisense

<400> SEQUENCE: 12
ttgcttccat cttcctcgtc                                              20
```

COMPOSITIONS AND METHODS FOR TOPICAL DELIVERY OF OLIGONUCLEOTIDES

CROSS REFERENCE TO RELATED APPLICATIONS

This application is a continuation of U.S. patent application Ser. No. 10/876,962, filed on Jun. 25, 2004, which application is a continuation of U.S. patent application Ser. No. 09/315294, filed on May 20, 1999, now U.S. Pat. No. 6,841,539, which is a continuation-in-part of U.S. patent application Ser. No. 09/082,336 filed on May 21, 1998, now abandoned, the disclosure of each of which is incorporated herein by reference in its entirety.

FIELD OF THE INVENTION

The present invention relates to new compositions and methods for the topical delivery of nucleic acids to the epidermis, the dermis, and strata therein, of animals. More particularly, the present invention is directed to the use of liposomes and penetration enhancers to effect transport of oligonucleotides and other nucleic acids into the epidermis and dermis. More specific objectives and advantages of the invention will hereinafter be made clear or become apparent to those skilled in the art during the course of explanation of preferred embodiments of the invention.

BACKGROUND OF THE INVENTION

Due to recent advances in biotechnology, particularly in the field of molecular biology, there has been significant progress in the treatment of diseases previously intractable, including cancers, genetic diseases, autoimmune disorders and AIDS. Many of these advances are achieved through the administration of nucleic acid molecules to a subject, often human. Often the administered nucleic acids are oligonucleotides.

The present invention is particularly drawn to compositions and methods for modulating the production of selected proteins or other biological effectors in an animal, which involves the administration of nucleic acids, including oligonucleotides such as, for example, antisense oligonucleotides, to the dermis and epidermis of an animal.

Various modes of administration of oligonucleotides to subjects have been shown to be effective for delivery of oligonucleotides to particular tissues or organs for the treatment of several diseases and/or disorders. For example, U.S. Pat. No. 5,595,978, issued Jan. 21, 1997, to Draper et al., discloses intravitreal injection as a means for the direct delivery of antisense oligonucleotides to the vitreous humor of the mammalian eye for the purpose of treating viral infections thereof. To date, however, attempts to effectively deliver oligonucleotides to the dermis and epidermis have not been realized.

The topical administration of oligonucleotides offers the promise of simpler, easier, and more effective delivery of nucleic acids to the epidermis and dermis without the need for sterile procedures and their concomitant expenses (e.g., hospitalization, physician fees, etc.). Thus, there is a need to provide compositions and methods for the topical delivery of oligonucleotides to the epidermis and dermis, and to selected strata therein, of an animal. It is desirable that such novel compositions and methods provide for the simple, efficient and convenient delivery of therapeutic nucleic acids, especially oligonucleotides.

SUMMARY OF THE INVENTION

In accordance with the present invention, compositions and methods are provided for topical delivery of nucleic acids in an animal. In particular, the present invention provides compositions and methods for modulating the production of selected proteins or other biological effectors in an animal, which involves the administration of an oligonucleotide, especially an antisense oligonucleotide, via topical means to an animal, thereby circumventing the complications and expense which may be associated with intravenous and other parenteral modes of in vivo administration.

"Topical administration" refers to the delivery of a nucleic acid to an animal by contacting, directly or otherwise, a formulation comprising the oligonucleotide to all or a portion of the skin (epidermis) of an animal. The term encompasses several routes of administration including, but not limited to, topical and transdermal. A common requirement for these modes of administration is penetration of the skin's permeability barrier and efficient delivery to the target tissue or stratum. In one aspect, topical administration is used as a means to penetrate the epidermis and dermis and ultimately achieve systemic delivery of oligonucleotides. In another aspect, topical administration is used as a means to selectively deliver oligonucleotides to the epidermis or dermis of an animal, or to specific strata thereof.

Compositions of the present invention may be a mixture of components or phases as are present in emulsions (including microemulsions and creams), and related formulations comprising two or more phases. In one aspect, the pharmaceutical compositions of the invention comprise a plurality of at least one type of nucleic acid and a plurality of at least one type of liposome. In certain embodiments, the nucleic acid is encapsulated, i.e., contained within the liposomes, while in others the nucleic acid is mixed with preformed liposomes to achieve an uncharacterized, presumably external, configuration with the liposomes; certain compositions of the invention comprise both types of [liposome:nucleic acid] configurations.

As detailed infra, the nucleic acid formulated in the pharmaceutical compositions of the invention can be, for example, an antisense oligonucleotide, a ribozyme, a peptide nucleic acid (PNA), an external guide sequence (EGS), a molecular decoy or an aptamer. The liposome portion of the pharmaceutical compositions of the invention can be a neutral liposome, an anionic liposome, or a anionic fusogenic liposome. Preferred liposomes are formed from one or more phospholipids, such as dimyristoyl phosphatidylcholine, dipalmitoyl phosphatidylcholine, dimyristoyl phosphatidylglycerol, or dioleoyl phosphatidylethanolamine. Particularly preferred liposomes are formed from a phospholipid, phosphatidylcholine derived from some natural source or a synthetic phosphatidylcholine molecule (hereinafter referred to in general as "phosphatidylcholine"), and a sterol such as, e.g., cholesterol. In general, the liposome is present in an amount which is effective to deliver the nucleosidic moiety to dermal or epidermal tissue in an animal.

In another aspect, the pharmaceutical compositions of the invention comprise at least one nucleosidic moiety and at least one penetration enhancer for enhancing penetration of the nucleosidic moiety into dermal or epidermal tissue in an animal. Representative penetration enhancers include fatty acids (such as isopropyl myristate), bile salts, chelating agents, surfactants, and non-surfactants (such as unsaturated cyclic ureas, 1-alkyl-alkanones, 1-alkenylazacyclo-alakanones, and steroidal anti-inflammatory agents), glycols, pyrrols, 1-acylazacycloheptan-2-ones ("azones"), and terpenes.

Also provided are methods for delivering nucleosidic moieties to dermal or epidermal tissue in an animal comprising one of the applying a pharmaceutical composition of the invention to epidermal tissue. In certain methods, the nucleosidic moiety is delivered preferentially to cells of the dermal tissue, while in other methods the nucleosidic moiety is delivered preferentially to cells of the epidermal tissue.

Because of the advantages of topical delivery of drugs of the antisense class, the compositions and methods of the invention can be used in therapeutic methods as explained in more detail herein. The compositions and methods herein provided may also be used to examine the function of various proteins and genes in vitro in cultured or preserved dermal tissues and in animals. The invention can be thus applied to examine the function of any gene, including, in animal other than a human, those essential to animal development. The methods of the invention can also be used therapeutically or prophylactically, for example, for the treatment of animals that are known or suspected to suffer from diseases such as psoriasis, lichen planus, toxic epidermal necrolysis, ertythema multiforme, basal cell carcinoma, squamous cell carcinoma, malignant melanoma, Paget's disease, Kaposi's sarcoma, pulmonary fibrosis, Lyme disease and viral, fungal and bacterial infections of the skin.

BRIEF DESCRIPTION OF THE FIGURES

The numerous objects and advantages of the present invention can be better understood by those skilled in the art by reference to the accompanying figures, in which:

FIGS. 1 and 2 show in tabular form results of epidermal and dermal delivery of oligonucleotides with various vehicle enhancers.

DETAILED DESCRIPTION OF THE INVENTION

I. Overview

The invention is drawn to the topical administration of a nucleic acid, such as an oligonucleotide, having biological activity in an animal. By "having biological activity," it is meant that the nucleic acid functions to modulate the expression of one or more genes in an animal as reflected in either absolute function of the gene (such as ribozyme activity) or by production of proteins coded by such genes. In the context of this invention, "to modulate" means to either effect an increase (stimulate) or a decrease (inhibit) in the expression of a gene. Such modulation can be achieved by, for example, an antisense oligonucleotide by a variety of mechanisms known in the art, including but not limited to transcriptional arrest; effects on RNA processing (capping, polyadenylation and splicing) and transportation; enhancement or reduction of cellular degradation of the target nucleic acid; and translational arrest (Crooke et al., *Exp. Opin. Ther. Patents*, 1996, 6:1).

The present invention provides methods and compositions for delivery of nucleic acids, particularly oligonucleotides, to the epidermis and/or dermis of an animal to increase the bioavailability of the nucleic acid therein. As used herein, the term "bioavailability" refers to the amount of the administered drug therapy (in this case the oligonucleotide) that reaches and acts upon its target. The term is used for drugs whose efficacy is measured relative to the concentration in the blood even though the ultimate site of action of the drug might be outside the blood, e.g., intracellular (see van Berge-Henegouwen et al., *Gastroenterology*, 1977, 73, 300).

The compositions and methods of the invention may be used to provide prophylactic, palliative or therapeutic relief from a disease or disorder that is treatable in whole or in part with one or more nucleic acids. In a preferred embodiment, such a disease or disorder is treatable in whole or in part via topical administration of an antisense oligonucleotide to an animal having such a disease or disorder.

As used in the present invention, unless specified otherwise, the term "animal" refers to mammals including but not limited to humans and primates; avians including chickens and turkeys; domestic household, sport or farm animals including dogs, cats, sheep, goats, cows, horses and pigs; lab animals including rats, mice, rabbits and guinea pigs; fish; reptiles; and zoo animals.

The term "skin," as used herein, refers to the epidermis and/or dermis of an animal. Mammalian skin consists of two major, distinct layers. The outer layer of the skin is called the epidermis. The epidermis is comprised of the stratum corneum, the stratum granulosum, the stratum spinosum, and the stratum basale, with the stratum corneum being at the surface of the skin and the stratum basale being the deepest portion of the epidermis. The epidermis is between 50 μm and 0.2 mm thick, depending on its location on the body.

Beneath the epidermis is the dermis, which is significantly thicker than the epidermis. The dermis is primarily composed of collagen in the form of fibrous bundles. The collagenous bundles provide support for, inter alia, blood vessels, lymph capillaries, glands, nerve endings and immunologically active cells.

One of the major functions of the skin as an organ is to regulate the entry of substances into the body. The principal permeability barrier of the skin is provided by the stratum corneum, which is formed from many layers of cells in various states of differentiation. The spaces between cells in the stratum corneum is filled with different lipids arranged in lattice-like formations which provide seals to further enhance the skin's permeability barrier.

The permeability barrier provided by the skin is such that it is largely impermeable to molecules having molecular weight greater than about 750 Da. For larger molecules to cross the skin's permeability barrier, mechanisms other than normal osmosis must be used. Consequently, there is a need for compositions and methods to facilitate the transport of nucleic acids through the skin's permeability barrier to the epidermis and the dermis.

Several factors determine the permeability of the skin to administered agents. These factors include the characteristics of the treated skin, the characteristics of the delivery agent, interactions between both the drug and delivery agent and the drug and skin, the dosage of the drug applied, the form of treatment, and the post treatment regimen. To selectively target the epidermis and dermis, it is sometimes possible to formulate a composition that comprises one or more penetration enhancers that will enable penetration of the drug to a preselected stratum.

A preferred method for the delivery of biologically active substances to the skin is topical administration. Topical administration can be used as the route of administration when local delivery of a drug is desired at, or immediately adjacent to, the point of application of the drug composition or formulation. Three general types of topical routes of administration include administration of a drug composition to mucous membranes, skin or eyes.

Transdermal drug delivery is a valuable route for the administration of lipid soluble therapeutics. The dermis is more permeable than the epidermis and therefore absorption is much more rapid through abraded, burned or denuded skin. Inflammation and other physiologic conditions that increase blood flow to the skin also enhance transdermal adsorption. Absorption via this route may be enhanced by the use of an oily vehicle (injunction) or through the use of one or more penetration enhancers. Other effective ways to deliver drugs via the transdermal route include hydration of the skin and the use of controlled release topical patches. The transdermal route provides a potentially effective means to deliver a drug for systemic and/or local therapy.

In addition, iontophoresis (transfer of ionic solutes through biological membranes under the influence of an electric field) (Lee et al., *Critical Reviews in Therapeutic Drug Carrier Systems,* 1991, p. 163), phonophoresis or sonophoresis (use of ultrasound to enhance the absorption of various therapeutic agents across biological membranes, notably the skin and the cornea) (Lee et al., *Critical Reviews in Therapeutic Drug Carrier Systems,* 1991, p. 166), and optimization of vehicle characteristics relative to dose deposition and retention at the site of administration (Lee et al., *Critical Reviews in Therapeutic Drug Carrier Systems,* 1991, p. 168) may be useful methods for enhancing the transport of drugs across mucosal sites in accordance with compositions and methods of the present invention.

II. Pharmaceutical Compositions

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The know-how on the preparation of such compositions and formulations is generally known to those skilled in the pharmaceutical and formulation arts and may be applied to the formulation of the compositions of the present invention.

A. Emulsions

The compositions of the present invention may be prepared and formulated as emulsions. Emulsions are typically heterogenous systems of one liquid dispersed in another in the form of droplets usually exceeding 0.1 um in diameter. (Idson, in *"Pharmaceutical Dosage Forms,"* Lieberman, Rieger and Banker (Eds.), 1988, volume 1, p. 199; Rosoff, in *"Pharmaceutical Dosage Forms,"* Lieberman, Rieger and Banker (Eds.), 1988, volume 1, p. 245; Block in *"Pharmaceutical Dosage Forms,"* Lieberman, Rieger and Banker (Eds.), 1988, volume 2, p. 335; Higuchi et al., in "Remington's Pharmaceutical Sciences," Mack Publishing Co., Easton, Pa., 1985, p. 301). Emulsions are often biphasic systems comprising of two immiscible liquid phases intimately mixed and dispersed with each other. In general, emulsions may be either water in oil (w/o) or of the oil in water (o/w) variety. When an aqueous phase is finely divided into and dispersed as minute droplets into a bulk oily phase the resulting composition is called a water in oil (w/o) emulsion. Alternatively, when an oily phase is finely divided into and dispersed as minute droplets into a bulk aqueous phase the resulting composition is called an oil in water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and antioxidants may also be present in emulsions as needed. Pharmaceutical emulsions may also be multiple emulsions that are comprised of more than two phases such as, for example, in the case of oil in water in oil (o/w/o) and water in oil in water (w/o/w) emulsions.

Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *"Pharmaceutical Dosage Forms,"* Lieberman, Rieger and Banker (Eds.), 1988, volume 1, p. 199).

Synthetic surfactants, also known as surface active agents, have found wide applicability in the formulation of emulsions and have been reviewed in the literature (Rieger, in *"Pharmaceutical Dosage Forms,"* Lieberman, Rieger and Banker (Eds.), 1988, volume 1, p. 285; Idson, in *"Pharmaceutical Dosage Forms,"* Lieberman, Rieger and Banker (Eds.), 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group into: nonionic, anionic, cationic and amphoteric (Rieger, in *"Pharmaceutical Dosage Forms,"* Lieberman, Rieger and Banker (Eds.), 1988, volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in "*Pharmaceutical Dosage Forms*," Lieberman, Rieger and Banker (Eds.), 1988, volume 1, p. 335; Idson, in "*Pharmaceutical Dosage Forms*," Lieberman, Rieger and Banker (Eds.), 1988, volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylc cellulose and carboxypropyl cellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methylparaben, propylparaben, quaternary ammonium salts, benzalkonium chloride, esters of p-hydroxybenzoic acid, boric acid and phenoxyethanol. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

Preservatives used in any oligonucleotide formulation will preferably have a broad spectrum of antimicrobial activity and be compatible with highly negatively charged oligonucleotides at neutral pH. To determine preferred preservatives, oligonucleotides were incubated with various preservatives in the presence and absence of selected organisms [*Staphylococcus aureus* (ATCC No. 6538), *Escherichia coli* (ATCC No. 8739), *Candida albicans* (ATCC No. 10231) and *Aspergillus niger* (ATCC No. 16404)] according to USP 23 Antimicrobial Effectiveness Test (AET) procedures. According to results of these studies it has been discovered that preferred preservatives for oligonucleotide formulations include a combination of methylparaben, propylparaben and phenoxyethanol. The total amount of the preservative combination will depend on the dosage form used but will in general be from about 0.1% to 20% by weight. In topical emulsion compositions of the invention, the preservative combination will be present in an amount from about 0.1% to 10%, preferably 0.5% to 8% and more preferably 1% to 5%. In a preferred embodiment, methylparaben and propylparaben will each be present in an amount from about 0.1% to 1% and phenoxyethanol in an amount from about 1 to 5%. In a particularly preferred embodiment methylparaben, propylparaben and phenoxyethanol will be present in a ratio of about 1:1:5 respectively.

The application of emulsion formulations via dermatological, oral and parenteral routes and methods for their manufacture have been reviewed in the literature (Idson, in "*Pharmaceutical Dosage Forms*," Lieberman, Rieger and Banker (Eds.), 1988, volume 1, p. 199). Emulsion formulations for oral delivery have been very widely used because of reasons of ease of formulation, efficacy from an absorption and bioavailability standpoint. (Rosoff, in "*Pharmaceutical Dosage Forms*," Lieberman, Rieger and Banker (Eds.), 1988, volume 1, p. 245; Idson, in "*Pharmaceutical Dosage Forms*," Lieberman, Rieger and Banker (Eds.), 1988, volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in "*Pharmaceutical Dosage Forms*," Lieberman, Rieger and Banker (Eds.), 1988, volume 1, p. 545). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in "Remington's Pharmaceutical Sciences," Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in "*Pharmaceutical Dosage Forms*," Lieberman, Rieger and Banker (Eds.), 1988, volume 1, p. 245; Block, in "*Pharmaceutical Dosage Forms*," Lieberman, Rieger and Banker (Eds.), 1988, volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO0750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research,* 1994, 11, 1385; Ritschel, *Meth. Find. Exp. Clin. Pharmacol.,* 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research,* 1994, 11, 1385; Ho et al., *J. Pharm. Sci.,* 1996, 85, 138). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems,* 1991, p. 92). Each of these classes has been discussed above.

In a particularly preferred embodiment, emulsion compositions comprise isopropyl myristate (IPM) as an emollient. IPM emulsions of the invention may be in cream form and incorporate IPM in an amount from about 1% to 50% by weight, more preferably 5% to 20% and most preferably about 10%. In preferred cream emulsions, glycerol monostearate serves as the oil phase emulsifier while polyoxyl 40 stearate serves as the water phase emulsifier, each present in an amount from about 1% to 30% and more preferably 5% to 20%. In a particularly preferred embodiment, glycerol monostearate is present in an amount of about 10% by weight and polyoxyl 40 stearate in an amount of about 15%. Preferred cream emulsions may further comprise viscosity-increasing agents such as hydroxypropyl methylcellulose. In a particularly preferred embodiment, hydroxypropyl methylcellulose is present in an amount from about 0.01% to about 5%, more preferably from 0.1% to 2% and most preferably about 0.5%.

B. Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently-with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly transformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *"Pharmaceutical Dosage Forms,"* Lieberman, Rieger and Banker (Eds.), 1988, volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell's cytoplasm (Wang et al., *Biochem. Biophys. Res. Commun.,* 147 (1987) 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 19, (1992) 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., Journal of Drug Targeting, 1992, Vol. 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 18, 1992, 259-265).

Non-ionic liposomal systems have also been examined to determine their utility in the delivery of drugs to the skin, in particular systems comprising non-ionic surfactant and cholesterol. Non-ionic liposomal formulations comprising Novasome" I (glyceryl dilaurate/cholesterol/polyoxyethylene-10-stearyl ether) and Novasome" II (glyceryl disterate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes.

The-most common way of classifying and ranking the properties of the many different types of surfactants, both natural and synthetic, is by the use of the hydrophile/lipophile balance (HLB). The nature of the hydrophilic group (also known as the 'head') provides the most useful means for categorizing the different surfactants used in formulations (Rieger, in "Pharmaceutical Dosage Forms," Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in "Pharmaceutical Dosage Forms," Marcel Dekker, Inc., New York, N.Y., 1988, p. 285).

C. Penetration Enhancers

In one embodiment, the present invention employ's various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Crit. Rev. Ther. Drug Carrier Systems, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Crit. Rev. Ther. Drug Carrier Systems, 1991, p. 92); and perfluorhemical emulsions, such as FC-43 Takahashi et al., *J. Pharm. Pharmacol.*, 1988, 40:252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Crit. Rev. Ther. Drug Carrier Systems, 1991, p. 92; Muranishi, Crit. Rev. Ther. Drug Carrier Systems, 1990, 7:1; El Hariri et al., J. Pharm. Pharmacol., 1992, 44:651).

Bile salts: The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, New York, 1996, pages 934-935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782-783; Muranishi, *Critical Reviews in Therapeutic Drug Carrier Systems*, 1990, 7:1; Yamamoto et al., *J. Pharm. Exp. Ther.*, 1992, 263:25; Yamashita et al., *J. Pharm. Sci.*, 1990, 79:579).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems*, 1991, page 92; Muranishi, *Critical Reviews in Therapeutic Drug Carrier Systems*, 1990, 7:1; Buur et al., *J. Control Rel.*, 1990, 14:43).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7:1). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39:621).

Agents that enhance uptake of oligonucleotides at the cellular level may also be added to the pharmaceutical and other compositions of the present invention. For example, cationic lipids, such as lipofectin (Junichi et al, U.S. Pat. No. 5,705, 188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

D. Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115; Takakura et al., *Antisense & Nucl. Acid Drug Dev.*, 1996, 6, 177).

E. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

F. Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings flavorings and/or aromatic substances and the like which do not deleteriously interact with the nucleic acid(s) of the formulation.

Aqueous suspensions may contain substances which increase the viscosity of the suspension including, for example, hydroxypropyl methylcellulose, sodium carboxymethylcellulose, sorbitol and/or dextran. The suspension may also contain stabilizers.

III. Oligonucleotides

The present invention employs pharmaceutical compositions comprising biologically active oligonucleotides useful for prophylactic, palliative or therapeutic purposes and, in isolated tissues or organs or in an animal other than a human, for investigative use. Typically, the formulations of the invention will comprise an oligonucleotide in an amount of from about 0.005 ng/mL to about 400 mg/mL, preferably from about 0.01 ng/mL to about 200 mg/mL, most preferably from about 0.1 ng/mL to about 100 mg/mL, where "about" indicates ±5% of the indicated concentration.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

A discussion of antisense oligonucleotides and some desirable modifications can be found in De Mesmaeker et al. (*Acc. Chem. Res.*, 1995, 28, 366). Generally, oligonucleotides formulated in the compositions of the invention may be from about 8 to about 100 nucleotides in length, more preferably from about 10 to about 50 nucleotides in length, and most preferably from about 10 about 25 nucleotides in length.

Oligonucleotides that are formulated in the compositions of the invention include (1) antisense compounds and (2) other bioactive oligonucleotides. These compounds are described in more detail, infra.

A. Antisense Compounds: As used herein, the term "antisense compound" encompasses, inter alia, antisense oligonucleotides, antisense peptide nucleic acids (PNAs), ribozymes and EGSs (described infra). In antisense modulation of messenger RNA (mRNA), hybridization of an antisense compound with its mRNA target interferes with the normal role of mRNA and causes a modulation of its function in cells. The functions of mRNA to be interfered with include all vital functions such as translocation of the RNA to the site for protein translation, actual translation of protein from the RNA, splicing of the RNA to yield one or more mRNA species, turnover or degradation of the mRNA and possibly even independent catalytic activity which may be engaged in by the RNA. The overall effect of such interference with mRNA function is modulation of the expression of a protein, wherein "modulation" means either an increase (stimulation) or a decrease (inhibition) in the expression of the protein. In the context of the present invention, inhibition is the preferred form of modulation of gene expression.

Antisense compounds can exert their effect by a variety of means. One such means is the antisense-mediated direction of an endogenous nuclease, such as RNase H in eukaryotes or RNase P in prokaryotes, to the target nucleic acid (Chiang et al., *J. Biol. Chem.*, 1991, 266, 18162; Forster et al., *Science*, 1990, 249, 783). The sequences that recruit RNase P are known as External Guide Sequences, hence the abbreviation "EGS" (Guerrier-Takada et al., *Proc. Natl. Acad. Sci. USA*, 1997, 94, 8468). Another means involves covalently linking a synthetic moiety having nuclease activity to an oligonucleotide having an antisense sequence, rather than relying upon recruitment of an endogenous nuclease. Synthetic moieties having nuclease activity include, but are not limited to, enzymatic RNAs, lanthanide ion complexes, and the like (Haseloff et al., Nature, 1988, 334, 585; Baker et al., *J. Am. Chem. Soc.*, 1997, 119, 8749).

As used herein, the term "antisense compound" also includes ribozymes, synthetic RNA molecules and derivatives thereof that catalyze highly specific endoribonuclease reactions (see, generally, U.S. Pat. No. 5,543,508 to Haseloff et al. and U.S. Pat. No. 5,545,729 to Goodchild et al.). The cleavage reactions are catalyzed by the RNA molecules themselves. In naturally occurring RNA molecules, the sites of self-catalyzed cleavage are located within highly conserved regions of RNA secondary structure (Buzayan et al., *Proc. Natl. Acad. Sci. USA*, 1986, 83, 8859; Forster et al., *Cell*, 1987, 50, 9). Naturally occurring autocatalytic RNA molecules have been modified to generate ribozymes which can be targeted to a particular cellular or pathogenic RNA molecule with a high degree of specificity. Thus, ribozymes serve the same general purpose as antisense oligonucleotides (i.e., modulation of expression of a specific gene) and, like oligonucleotides, are nucleic acids possessing significant portions of single-strandedness. That is, ribozymes have substantial chemical and functional identity with other bioactive compounds and may thus be formulated for pharmaceutical delivery using the liposomes of the present invention.

The antisense compounds formulated in the compositions of the invention (1) may be from about 8 to about 100 nucleotides in length, more preferably from about 10 to about 30 nucleotides in length, (2) are targeted to a nucleic acid sequence required for the expression of a gene from a mammal, including a human, and (3), when contacted with cells expressing the target gene, modulate its expression. Due to the biological activity of the gene product encoded by the target gene, modulation of its expression has the desirable result of providing specific prophylactic, palliative and/or therapeutic effects.

B. Other Bioactive Oligonucleotides: The term "Other Bioactive Oligonucleotide" encompasses, inter alia, aptamers and molecular decoys (described infra). As used herein, the term is meant to refer to any oligonucleotide (including a PNA) that (1) provides a prophylactic, palliative or therapeutic effect to an animal in need thereof and (2) acts by a non-antisense mechanism, i.e., by some means other than by hybridizing to a nucleic acid.

The name aptamer has been coined by Ellington et al. (*Nature,* 1990, 346, 818) to refer to nucleic acid molecules that fit and therefore bind with significant specificity to non-nucleic acid ligands such as peptides, proteins and small molecules such as drugs and dyes. Because of these specific ligand binding properties, nucleic acids and oligonucleotides that may be classified as aptamers may be readily purified or isolated via affinity chromatography using columns that bear immobilized ligand. Aptamers may be nucleic acids that are relatively short to those that are as large as a few hundred nucleotides. For example, RNA aptamers that are 155 nucleotides long and that bind dyes such as Cibacron Blue and Reactive Blue 4 with good selectivity have been reported (Ellington et al., *Nature,* 1990, 346, 818). While RNA molecules were first referred to as aptamers, the term as used in the present invention refers to any nucleic acid or oligonucleotide that exhibits specific binding to small molecule ligands including, but not limited to, DNA, RNA, DNA derivatives and conjugates, RNA derivatives and conjugates, modified oligonucleotides, chimeric oligonucleotides, and gapmers (see, e.g., U.S. Pat. No. 5,523,389, to Ecker et al., issued Jun. 4, 1996 and incorporated herein by reference).

Molecular decoys are short double-stranded nucleic acids (including single-stranded nucleic acids designed to "fold back" on themselves) that mimic a site on a nucleic acid to which a factor, such as a protein, binds. Such decoys are expected to competitively inhibit the factor; that is, because the factor molecules are bound to an excess of the decoy, the concentration of factor bound to the cellular site corresponding to the decoy decreases, with resulting therapeutic, palliative or prophylactic effects. Methods of identifying and constructing decoy molecules are described in, e.g., U.S. Pat. No. 5,716,780 to Edwards et al.

Another type of bioactive oligonucleotide is an RNA-DNA hybrid molecule that can direct gene conversion of an endogenous nucleic acid (Cole-Strauss et al., *Science,* 1996, 273, 1386). Any of the preceding bioactive oligonucleotides may be formulated in the liposomes of the invention and used for prophylactic or therapeutic purposes.

C. Oligonucleotide Modifications

An oligonucleotide is a polymer of a repeating unit generically known as a nucleotide. An unmodified (naturally occurring) nucleotide has three components: (1) a nitrogen-containing heterocyclic base linked by one of its nitrogen atoms to (2) a 5-pentofuranosyl sugar and (3) a phosphate esterified to one of the 5' or 3' carbon atoms of the sugar. When incorporated into an oligonucleotide chain, the phosphate of a first nucleotide is also esterified to an adjacent sugar of a second, adjacent nucleotide via a 3'-5' phosphate linkage.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be further joined to form a circular structure, however, within the context of the invention, open linear structures are generally preferred.

Within the oligonucleotide structure, the phosphate groups are commonly referred to as forming the intersugar "backbone" of the oligonucleotide. The normal linkage or backbone of RNA and DNA is a 3' to 5' phosphodiester linkage. The backbone of an oligonucleotide (or other antisense compound) positions a series of bases in a specific order; the written representation of this ordered series of bases, usually written in 5' to 3' order unless otherwise indicated, is known as a nucleotide or nucleobase sequence.

Oligonucleotides may comprise nucleotide sequences sufficient in identity and number to effect specific hybridization with a particular nucleic acid. Such oligonucleotides which specifically hybridize to a portion of the sense strand of a gene are commonly described as "antisense." In the context of the invention, "hybridization" means hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other.

"Specifically hybridizable" and "complementary" are thus terms which are used to indicate a sufficient degree of complementarity or precise pairing such that stable and specific binding occurs between the oligonucleotide and the DNA or RNA target. An oligonucleotide is specifically hybridizable to its target sequence due to the formation of base pairs between specific partner nucleobases in the interior of a nucleic acid duplex. Among the naturally occurring nucleobases, guanine (G) binds to cytosine (C), and adenine (A) binds to thymine (T) or uracil (U). In addition to the equivalency of U (RNA) and T (DNA) as partners for A, other naturally occurring nucleobase equivalents are known, including 5-methylcytosine and 5-hydroxymethylcytosine (HMC) (C equivalents), and 5-hydroxymethyluracil (U equivalent). Furthermore, synthetic nucleobases which retain partner specificity are known in the art and include, for example, 7-deaza-Guanine, which retains partner specificity for C. Thus, an oligonucleotide's capacity to specifically hybridize with its target sequence will not be altered by a chemical modification to a nucleobase in the nucleotide sequence of the oligonucleotide which does not impact its specificity for a partner nucleobase in the target nucleic acid.

It is understood in the art that the nucleobase sequence of an oligonucleotide or other antisense compound need not be 100% complementary to its target nucleic acid sequence to be specifically hybridizable. An antisense compound is specifically hybridizable to its target nucleic acid when there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under assay conditions.

Antisense oligonucleotides are commonly used as research reagents, diagnostic aids, and therapeutic agents.

For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed by those skilled in the art for research uses. The specificity and sensitivity of oligonucleotides is also harnessed by those of skill in the art for therapeutic uses. Specific examples of preferred antisense compounds useful in this invention include oligonucleotides containing modified backbones or non-natural intersugar linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their intersugar backbone can also be considered to be oligonucleosides.

Specific oligonucleotide chemical modifications are described in the following subsections. It is not necessary for all positions in a given compound to be uniformly modified, and in fact more than one of the following modifications may be incorporated in a single antisense compound or even in a single residue thereof, for example, at a single nucleoside within an oligonucleotide.

Modified Linkages: Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalklyphosphotriesters, and boranbphosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States Patents that teach the preparation of the above phosphorus atom containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 25 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, certain of which are commonly owned with this application, and each of which is herein incorporated by reference.

Preferred modified oligonucleotide backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

In other preferred oligonucleotide mimetics, both the sugar and the intersugar linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al. (*Science,* 1991, 254, 1497).

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [(wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Nucleobases: The compounds of the invention may additionally or alternatively comprise nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Id., pages 276-278) and are presently preferred base substitutions, even more particularly when combined with 2'-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, certain of which are commonly owned, and each of which is herein incorporated by reference, and commonly owned U.S. patent application Ser. No. 08/762,488, filed on Dec. 10, 1996, also herein incorporated by reference.

Sugar Modifications: The antisense compounds of the invention may additionally or alternatively comprise one or more substituted sugar moieties. Preferred oligonucleotides comprise one of the following at the 2' position: OH; F; O—, S—, or N-alkyl, O—, S—, or N-alkenyl, or O, S— or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy [2'-O—$CH_2CH_2OCH_3$, also known as 2'-O—(2-methoxyethyl) or 2'-MOE] (Martin et al., *Helv. Chim. Acta*, 1995, 78, 486), i.e., an alkoxyalkoxy group. A further preferred modification includes 2'-dimethylaminooxyethoxy, i.e., a $O(CH_2)_2ON(CH_3)_2$ group, also known as 2'-DMAOE, as described in co-owned U.S. patent application Ser. No. 09/016,520, filed on Jan. 30, 1998, the contents of which are herein incorporated by reference.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319, 080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, also herein incorporated by reference.

Other Modifications: Additional modifications may also be made at other positions on the oligonucleotide, particularly the 3' position of the sugar on the 3' terminal nucleotide and the 5' position of 5' terminal nucleotide. For example, one additional modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned, and each of which is herein incorporated by reference.

Chimeric Oligonucleotides: The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate oligodeoxynucleotides hybridizing to the same target region. Cleavage of the RNA target can be routinely detected by gel electrophoresis and, if necessary, associated nucleic acid hybridization techniques known in the art. RNase H-mediated target cleavage is distinct from the use of ribozymes to cleave nucleic acids, and ribozymes are not comprehended by the present invention.

By way of example, such "chimeras" may be "gapmers," i.e., oligonucleotides in which a central portion (the "gap") of the oligonucleotide serves as a substrate for, e.g., RNase H, and the 5' and 3' portions (the "wings") are modified in such a fashion so as to have greater affinity for, or stability when duplexed with, the target RNA molecule but are unable to support nuclease activity (e.g., 2'-fluoro- or 2'-methoxyethoxy-substituted). Other chimeras include "hemimers," that is, oligonucleotides in which the 5' portion of the oligonucleotide serves as a substrate for, e.g., RNase H, whereas the 3' portion is modified in such a fashion so as to have greater affinity for, or stability when duplexed with, the target RNA molecule but is unable to support nuclease activity (e.g., 2'-fluoro- or 2'-methoxyethoxy-substituted), or vice-versa.

A number of chemical modifications to oligonucleotides that confer greater oligonucleotide:RNA duplex stability have been described by Freier et al. (*Nucl. Acids Res.,* 1997, 25, 4429). Such modifications are preferred for the RNase H-refractory portions of chimeric oligonucleotides and may generally be used to enhance the affinity of an antisense compound for a target RNA.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned, and each of which is herein incorporated by reference, and commonly owned and allowed U.S. patent application Ser. No. 08/465,880, filed on Jun. 6, 1995, also herein incorporated by reference.

A further preferred modification includes 2'-dimethylamino oxyethoxy, i.e., a $O(CH_2)_2ON(CH_3)_2$ group, also known as 2'-DMAOE, as described in co-owned U.S. patent application Ser. No. 09/016,520, filed on Jan. 30, 1998, the contents of which are herein incorporated by reference. Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the sugar group, particularly the 3' position of the sugar on the 3' terminal nucleotide or in 2'-5' linked oligonucleotides and the 5' position of 5' terminal nucleotide. The nucleosides of the oligonucleotides may also have sugar mimetics such as cyclobutyl moieties in place of the pentofuranosyl sugar.

Unsubstituted and substituted phosphodiester oligonucleotides are alternately synthesized on an automated DNA synthesizer (Applied Biosystems model 380B) using standard phosphoramidite chemistry with oxidation by iodine.

Phosphorothioates are synthesized as per the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step.. After cleavage from the CPG column and deblocking in concentrated ammonium hydroxide at 55° C. (18 hr), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. Nos. 5,256,775 or 5,366,878, hereby incorporated by reference.

Alkylphosphonothioate oligonucleotides are prepared as described in published PCT applications PCT/US94/00902 and PCT/US93/06976 (published as WO 94/17093 and WO 94/02499, respectively).

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Boranophosphate oligonucleotides are prepared as described in U.S. Pat. Nos. 5,130,302 and 5,177,198, both herein incorporated by reference.

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and PO or PS linkages are prepared as described in U.S. Pat. Nos. 5,378,825; 5,386,023; 5,489,677; 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Peptide nucleic acids (PNAs) are prepared in accordance with any of the various procedures referred to in Peptide Nucleic Acids (PNA): Synthesis, Properties and Potential Applications, *Bioorganic & Medicinal Chemistry,* 1996, 4, 5. They may also be prepared in accordance with U.S. Pat. Nos. 5,539,082; 5,700,922, and 5,719,262, herein incorporated by reference.

Examples of specific oligonucleotides and the target genes which they inhibit, that may be employed in formulations of the present invention include:

```
ISIS-2302
GCCCA AGCTG GCATC CGTCA      (SEQ ID NO: 1)    ICAM-1

ISIS-15839
GCCCA AGCTG GCATC CGTCA      (SEQ ID NO: 1)    ICAM-1

ISIS-1939
CCCCC ACCAC TTCCC CTCTC      (SEQ ID NO: 2)    ICAM-1

ISIS-2503
TCCGT CATCG CTCCT CAGGG      (SEQ ID NO: 4)    Ha-ras

ISIS-2922
GCGTT TGCTC TTCTT CTTGC G    (SEQ ID NO: 5)    HCMV

ISIS-13312
GCGTT TGCTC TTCTT CTTGC G    (SEQ ID NO: 5)    HCMV

ISIS-3521
GTTCT CGCTG GTGAG TTTCA      (SEQ ID NO: 6)    PKCα

ISIS-9605
GTTCT CGCTG GTGAG TTTCA      (SEQ ID NO: 6)    PKCα

ISIS-9606
GTTCT CGCTG GTGAG TTTCA      (SEQ ID NO: 6)    PKCα

ISIS-14859
AACTT GTGCT TGCTC            (SEQ ID NO: 7)    PKCα

ISIS-5132
TCCCG CCTGT GACAT GCATT      (SEQ ID NO: 8)    c-raf

ISIS-14803
GTGCT CATGG TGCAC GGTCT      (SEQ ID NO: 9)    HCV

ISIS-28089
GTGTG CCAGA CACCC TATCT      (SEQ ID NO: 10)   TNFα

ISIS-104838
GCTGA TTAGA GAGAG GTCCC      (SEQ ID NO: 11)   TNFα

ISIS-2105
TTGCT TCCAT CTTCC TCGTC      (SEQ ID NO: 12)   HPV
``` wherein (i) each oligo backbone linkage is a phosphorothioate linkage (except ISIS-9605) and (ii) each sugar is 2'-deoxy unless represented in bold font in which case it incorporates a 2'-O-methoxyethyl group and iii) underlined cytosine nucleosides incorporate a 5-methyl substituent on their nucleobase. ISIS-9605 incorporates natural phosphodiester bonds at the first five and last five linkages with the remainder being phosphorothioate linkages.

D. Synthesis of Oligonucleotides: The oligonucleotides used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides such as the phosphorothioates and alkylated derivatives.

Teachings regarding the synthesis of particular modified oligonucleotides may be found in the following U.S. patents or pending patent applications, each of which is commonly assigned with this application: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, issued Jun. 29, 1993, and U.S. Pat. No. 5,608,046, both drawn to conjugated 4'-desmethyl nucleoside analogs; U.S. Pat. Nos. 5,602,240, and 5,610,289, drawn to backbone modified oligonucleotide analogs; and U.S. patent application Ser. No. 08/383,666, filed Feb. 3, 1995, and U.S. Pat. No. 5,459,255, drawn to, inter alia, methods of synthesizing 2'-fluoro-oligonucleotides.

E. Bioequivalents: In addition to oligonucleotide drugs per se, the pharmaceutical compositions of the present invention can be used to formulate any pharmaceutically acceptable salts, esters, or salts of such esters, or any other compound which, upon administration to an animal including a human, is capable of providing (directly or indirectly) a biologically active oligonucleotide or residue thereof. Accordingly, for example, the disclosure is also drawn to "prodrugs" and "pharmaceutically acceptable salts" of the oligonucleotides of the invention, pharmaceutically acceptable salts of such prodrugs, and other bioequivalents.

Oligonucleotide Prodrugs: The oligonucleotide and nucleic acid compounds employed in the compositions of the present invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the antisense compounds may be prepared as SATE [(S-acetyl-2-thioethyl)phosphate] derivatives according to the methods disclosed in WO 93/24510 (Gosselin et al., published Dec. 9, 1993).

Pharmaceutically Acceptable Salts: The term "pharmaceutically acceptable salts" refers to physiologically and pharmaceutically acceptable salts of the oligonucleotide and nucleic acid compounds employed in the compositions of the present invention (i.e., salts that retain the desired biological activity of the parent compound and do not impart undesired toxicological effects thereto).

Pharmaceutically acceptable base addition salts are formed with metals or amines, such as alkali and alkaline earth metals or organic amines. Examples of metals used as cations are sodium, potassium, magnesium, calcium, ammonium, polyamines such as spermine and spermidine, and the like. Examples of suitable amines are chloroprocaine, choline, N,N'-dibenzylethylenediamine, diethanolamine, dicyclohexylamine, ethylenediamine, N-methylglucamine, and procaine (see, for example, Berge et al., "Pharmaceutical Salts," *J. of Pharma Sci.*, 1977, 66:1). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

n-1 Derivatives: During the process of oligonucleotide synthesis, nucleoside monomers are attached to the chain one at a time in a repeated series of chemical reactions such as nucleoside monomer coupling, oxidation, capping and detritylation. The stepwise yield for each nucleoside addition is above 99%. That means that less than 1% of the sequence chain failed to be generated from the nucleoside monomer addition in each step as the total results of the incomplete coupling followed by the incomplete capping, detritylation and oxidation (Smith, *Anal. Chem.*, 1988, 60, 381A). All the shorter oligonucleotides, ranging from (n-1), (n-2), etc., to 1-mers (nucleotides), are present as impurities in the n-mer olignucleotide product. Among the impurities, (n-2)-mer and shorter oligonucleotide impurities are present in very small amounts and can be easily removed by chromatographic purification (Warren et al., Chapter 9 In: *Methods in Molecular Biology*, Vol. 26: *Protocols for Oligonucleotide Conjugates*, Agrawal, S., Ed., 1994, Humana Press Inc., Totowa, N.J., pages 233-264). However, due to the lack of chromatographic selectivity and product yield, some (n-1)-mer impurities are still present in the full-length (i.e., n-mer) oligonucleotide product after the purification process. The (n-1) portion consists of the mixture of all possible single base deletion sequences relative to the n-mer parent oligonucleotide. Such (n-1) impurities can be classified as terminal deletion or internal deletion sequences, depending upon the position of the missing base (i.e., either at the 5' or 3' terminus or internally). When an oligonucleotide containing single base deletion sequence impurities is used as a drug (Crooke, *Hematologic Pathology*, 1995, 9, 59), the terminal deletion sequence impurities will bind to the same target mRNA as the full length sequence but with a slightly lower affinity. Thus, to some extent, such impurities can be considered as part of the active drug component, and are thus considered to be bioequivalents for purposes of the present invention.

IV. Therapeutic Indications and Other Uses

Psoriasis: One therapeutic indication of particular interest for topical delivery of oligonucleotides and other nucleic acids is psoriasis. Psoriasis is a common chronic and recurrent disease characterized by dry, well-circumscribed, silvery, scaling papules and plaques of various sizes. The disease varies in severity from a few lesions to widespread dermatosis with disabling arthritis or exfoliation. The ultimate cause of psoriasis is not known, but the thick scaling that occurs is probably due to increased epidermal cell proliferation (*The Merck Manual of Diagnosis and Therapy*, 15th Ed., pp. 2283-2285, Berkow et al., eds., Rahway, N.J., 1987). Inhibitors of Protein Kinase C (PKC), ICAM-1 and tumour necrosis factor (TNFα) have been shown to have both antiproliferative and anti-inflammatory effects in vitro. Some antipsoriasis drugs, such as cyclosporin A and anthralin, have been shown to inhibit PKC, and inhibition of PKC has been suggested as a therapeutic approach to the treatment of psoriasis (Hegemann, L. and G. Mahrle, *Pharmacology of the Skin*, H. Mukhtar, ed., pp. 357-368, CRC Press, Boca Raton, Fla., 1992).

Antisense compounds targeted to Protein Kinase C (PKC) proteins are described in U.S. Pat. No. 5,620,963 to Cook et al. and U.S. Pat. No. 5,681,747 to Boggs et al.

Inflammations Another type of therapeutic indication of particular interest for topical modes of delivery includes inflammatory disorders of the skin. These occur in a variety of forms including, for example, lichen planus, toxic epidermal necrolyis (TEN), ertythema multiforme and the like (*The Merck Manual of Diagnosis and Therapy*, 15th Ed., pp. 2286-2292, Berkow et al., eds., Rahway, N.J., 1987). Expression of ICAM-1 has been associated with a variety of inflammatory skin disorders such as allergic contact dermatitis, fixed drug eruption, lichen planus and psoriasis (Ho et al., *J. Am. Acad. Dermatol.*, 1990, 22, 64; Griffiths et al., *Am. J. Pathology*, 1989, 135, 1045; Lisby et al., *Br. J. Dermatol.*, 1989, 120, 479; Shiohara et al., *Arch. Dermatol.*, 1989, 125, 1371; Regezi et al., *Oral Sure. Oral Med. Oral Pathol.*, 1996, 81, 682). Moreover, intraperitoneal administration of a monoclonal antibody to ICAM-1 decreases ovalbumin-induced eosinophil infiltration into skin in mice (Hakugawa et al., *J. Dermatol.*, 1997, 24, 73). Antisense compounds targeted to ICAM-1 are described in U.S. Pat. Nos. 5,514,788 and 5,591,623, and co-pending U.S. patent application Ser. Nos. 09/009,490 and 09/062,416, Jan. 20, 1998 and Apr. 17, 1998, respectively, all to Bennett et al.

Other antisense targets for skin inflammatory disorders are VCAM-1 and PECAM-1. Intraperitoneal administration of a monoclonal antibody to VCAM-1 decreases ovalbumin-induced eosinophil infiltration into the skin of mice (Hakugawa et al., *J. Dermatol.*, 1997, 24, 73). Antisense compounds targeted to VCAM-1 are described in U.S. Pat. Nos. 5,514,788 and 5,591,623. PECAM-1 proteins are glycoproteins which are expressed on the surfaces of a: variety of cell types (for reviews, see Newman, *J. Clin. Invest.*, 1997, 99, 3 and DeLisser et al., *Immunol. Today*, 1994, 15, 490). In addition to directly participating in cell-cell interactions, PECAM-1 apparently also regulates the activity and/or expression of other molecules involved in cellular interactions (Litwin et al., *J. Cell Biol.*, 1997, 139, 219) and is thus a key mediator of several cell:cell interactions. Antisense compounds targeted to PECAM-1 are described in co-pending U.S. patent application Ser. No. 09/044,506, filed Mar. 19, 1998, by Bennett et al.

Skin Cancers: Another type of therapeutic indication of interest for topical delivery of oligonucleotides encompasses a variety of cancers of the skin. Representative skin cancers include benign tumors (warts, moles and the like) and malignant tumors such as, for-example, basal cell carcinoma, squamous cell carcinoma, malignant melanoma, Paget's disease, Kaposi's sarcoma and the like (*The Merci Manual of Diagnosis and Therapy*, 15th Ed., pp. 2301-2310, Berkow et al., eds., Rahay, N.J., 1987). A number of molecular targets involved in tumorigenesis, maintenance of the hyperproliferative state and metastasis are targeted to prevent or inhibit skin cancers, or to prevent their spread to other tissues.

The ras oncogenes are guanine-binding proteins that have been implicated in cancer by, e.g., the fact that activated ras oncogenes have been found in about 30% of human tumors generally; this figure approached 100% in carcinomas of the exocrine pancreas (for a review, see Downward, *Trends in Biol. Sci.*, 1990, 15, 469). Antisense compounds targeted to H-ras and K-ras are described in U.S. Pat. No. 5,582,972 to Lima et al., U.S. Pat. No. 5,582,986 to Monia et al. and U.S. Pat. No. 5,661,134 to Cook et al., and in published PCT application WO 94/08003.

Protein Kinase C (PKC) proteins have also been implicated in tumorigenesis. Antisense compounds targeted to Protein Kinase C (PKC) proteins are described in U.S. Pat. No. 5,620,963 to Cook et al. and U.S. Pat. No. 5,681,747 to Boggs et al. Also of interest are AP-1 subunits and JNK proteins, particularly in regard to their roles in tumorigenesis and metastasis. The process of metastasis involves a sequence of events wherein (1) a cancer cell detaches from its extracellular matrices, (2) the detached cancer cell migrates to another portion of an animal's body, often via the circulatory system, and (3) attaches to a distal and inappropriate extracellular matrix, thereby created a focus from which a secondary tumor can arise. Normal cells do not possess the ability to invade or metastasize and/or undergo apoptosis (programmed cell death) if such events occur (Ruoslahti, *Sci. Amer.*, 1996, 275, 72). However, many human tumors have elevated levels of activity of one or more matrix metalloproteinases (MMPs) (Stetler-Stevenson et al., *Annu. Rev. Cell Biol.*, 1993, 9, 541; Bernhard et al., *Proc. Natl. Acad. Sci. (U.S.A.)*, 1994, 91, 4293. The MMPs are a family of enzymes which have the ability to degrade components of the extracellular matrix (Birkedal-Hansen, *Current Op. Biol.*, 1995, 7, 728). In particular, one member of this family, matrix metalloproteinase-9 (MMP-9), is often found to be expressed only in tumors and other diseased tissues (Himelstein et al., *Invasion & Metastasis*, 1994, 14, 246).

Several studies have shown that regulation of the MMP-9 gene may be controlled by the AP-1 transcription factor (Kerr et al., *Science*, 1988, 242, 1242; Kerr et al., *Cell*, 1990, 61, 267; Gum et al., *J. Biol. Chem.*, 1996, 271, 10672; Hua et al., *Cancer Res.*, 1996, 56, 5279). Inhibition of AP-1 function has been shown to attenuate MMP-9 expression (U.S. patent application Ser. No. 08/837,201). AP-1 is a heterodimeric protein having two subunits, the gene products of fos and jun. Antisense compounds targeted to c-fos and c-jun are described in co-pending U.S. patent application Ser. No. 08/837,201, filed Mar. 14, 1997, by Dean et al.

Furthermore, AP-1 is itself activated in certain circumstances by phosphorylation of the Jun subunit at an aminoterminal position by Jun N-terminal kinases (JNKs). Thus, inhibition of one or more JNKs is expected to result in decreased AP-1 activity and, consequentially, reduced MMP expression. Antisense compounds targeted to JNKs are described in co-pending U.S. patent application Ser. No. 08/910,629, filed Aug. 13, 1997, by Dean et al.

Infectious Diseases of the Skins Also of interest for topical formulations of oligonucleotides are infectious diseases of the skin. Such infections are caused by viral, bacterial or fungal agents.

In the case of Lyme disease, the tick borne causative agent thereof, the spirochete *Borrelia burgdorferi*, up-regulates the expression of ICAM-1, VCAM-1 and ELAM-1 on endothelial cells in vitro (Boggemeyer et al., *Cell Adhes. Comm.*, 1994, 2, 145). Furthermore, it has been proposed that the mediation of the disease by the anti-inflammatory agent prednisolone is due in part to mediation of this up-regulation of adhesion molecules (Hurtenbach et al., *Int. J. Immunopharmac.*, 1996, 18, 281). Thus, potential targets for therapeutic mediation (or prevention) of Lyme disease include ICAM-1, VCAM-1 and ELAM-1 (supra).

Other infectious disease of the skin which are tractable to treatment using the compositions and methods of the invention include disorders resulting from infection by bacterial, viral or fungal agents (*The Merck Manual of Diagnosis and Therapy*, 15th Ed., pp. 2263-2277, Berkow et al., eds., Rahay, N.J., 1987). With regards to infections of the skin caused by fungal agents, U.S. Pat. No. 5,691,461 provides antisense compounds for inhibiting the growth of *Candida albicans*.

With regards to infections of the skin caused by viral agents, U.S. Pat. Nos. 5,166,195, 5,523,389 and 5,591,600 provide oligonucleotide inhibitors of Human Immunodeficiency Virus (HIV). U.S. Pat. No. 5,004,810 provides oligomers capable of hybridizing to herpes simplex virus Vmw65 mRNA and inhibiting its replication. U.S. Pat. Nos. 5,194,428 and 5,580,767 provide antisense compounds having antiviral activity against influenza virus. U.S. Pat. No. 4,806,463 provides antisense compounds and methods using them to inhibit HTLV-III replication. U.S. Pat. Nos. 4,689,320, 5,442,049, 5,591,720 and 5,607,923 are directed to antisense compounds as antiviral agents specific to cytomegalovirus (CMV). U.S. Pat. No. 5,242,906 provides antisense compounds useful in the treatment of latent Epstein-Barr virus (EBV) infections. U.S. Pat. Nos. 5,248,670, 5,514,577 and 5,658,891 provide antisense compounds useful in the treatment of herpes virus infections. U.S. Pat. Nos. 5,457,189 and 5,681,944 provide antisense compounds useful in the treatment of papilloma virus infections. The antisense compounds disclosed in these patents, which are herein incorporated by reference, may be used with the compositions of the invention to effect prophylactic, palliative or therapeutic relief from diseases caused or exacerbated by the indicated pathogenic agents.

Investigative Uses: Antisense oligonucleotides employed in the compositions of the present invention may also be used to determine the nature, function and potential relationship of various genetic components of the body to disease or body states in animals. Heretofore, the function of a gene has been chiefly examined by the construction of loss-of-function mutations in the gene (i.e., "knock-out" mutations) in an animal (e.g., a transgenic mouse). Such tasks are difficult, time-consuming and cannot be accomplished for genes essential to animal development since the "knock-out" mutation would produce a lethal phenotype. Moreover, the loss-of-function phenotype cannot be transiently introduced during a particular part of the animal's life cycle or disease state; the "knock-out" mutation is always present. "Antisense knockouts," that is, the selective modulation of expression of a gene by antisense oligonucleotides, rather than by direct genetic manipulation, overcomes these limitations (see, for example, Albert et al., *Trends in Pharmacological Sciences*, 1994, 15, 250). In addition, some genes produce a variety of mRNA transcripts as a result of processes such as alternative splicing; a "knock-out" mutation typically removes all forms of mRNA transcripts produced from such genes and thus cannot be used to examine the biological role of a particular mRNA transcript. Antisense oligonucleotides have been systemically administered to rats in order to study the role of the N-methyl-D-aspartate receptor in neuronal death, to mice in order to investigate the biological role of protein kinase C-a, and to rats in order to examine the role of the neuropeptide Y1 receptor in anxiety (Wahlestedt et al., *Nature*, 1993, 363:260; Dean et al., *Proc. Natl. Acad. Sci. U.S.A.*, 1994, 91:11762; and Wahlestedt et al., *Science*, 1993, 259:528, respectively). In instances where complex families of related proteins are being investigated, "antisense knockouts" (i.e., inhibition of a gene by systemic administration of antisense oligonucleotides) may represent the most accurate means for examining a specific member of the family (see, generally, Albert et al., *Trends Pharmacol. Sci.*, 1994, 15:250). By providing compositions and methods for the simple non-parenteral delivery of oligonucleotides and other nucleic acids, the present invention overcomes these and other shortcomings.

V. Treatment Regimens

The administration of therapeutic or pharmaceutical compositions comprising the liposomes of the invention is believed to be within the skill of those in the art. In general, a patient in need of therapy or prophylaxis is administered a composition comprising a liposomally formulated bioactive agents in accordance with the invention, commonly in a pharmaceutically acceptable carrier, in doses ranging from 0.01 ug to 100 g per kg of body weight depending on the age of the patient and the severity of the disorder or disease state being treated. Dosing is dependent on severity and responsiveness of the disease state to be treated, with the course of treatment lasting from several days to several months, or until a cure is effected or a diminution or prevention of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual antisense compounds, and can generally be estimated based on $EC_{50}$s found to be effective in in vitro and in vivo animal models.

In the context of the invention, the term "treatment regimen" is meant to encompass therapeutic, palliative and prophylactic modalities of administration of one or more liposomal compositions of the invention. A particular treatment regimen may last for a period of time which will vary depending upon the nature of the particular disease or disorder, its severity and the overall condition of the patient, and may extend from once daily to once every 20 years. Following treatment, the patient is monitored for changes in his/her condition and for alleviation of the symptoms of the disorder or disease state. The dosage of the liposomal composition may either be increased in the event the patient does not respond significantly to current dosage levels, or the dose may be decreased if an alleviation of the symptoms of the disorder or disease state is observed, or if the disorder or disease state has been ablated.

An optimal dosing schedule is used to deliver a therapeutically effective amount of the bioactive agent encapsulated within the liposomes of the invention being administered via a particular mode of administration. The term "therapeutically effective amount," for the purposes of the invention, refers to the amount of oligonucleotide-containing pharmaceutical composition which is effective to achieve an intended purpose without undesirable side effects (such as toxicity, irritation or allergic response). Although individual needs may vary, determination of optimal ranges for effective amounts of pharmaceutical compositions is within the skill of the art. Human doses can be extrapolated from animal studies (Katocs et al., Chapter 27 In: *Remington's Pharmaceutical Sciences,* 18th Ed., Gennaro, ed., Mack Publishing Co., Easton, Pa., 1990). Generally, the dosage required to provide an effective amount of a pharmaceutical composition, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s) (Nies et al., Chapter 3 In: *Goodman & Gilman's The Pharmacological Basis of Therapeutics,* 9th Ed., Hardman et al., eds., McGraw-Hill, New York, N.Y., 1996).

Following successful treatment, it may be desirable to have the patient undergo maintenance therapy to prevent the recurrence of the disease state, wherein the bioactive agent is administered in maintenance doses, ranging from 0.01 ug to 100 g per kg of body weight, once or more daily, to once every years. For example, in the case of in individual known or suspected of being prone to an autoimmune or inflammatory condition, prophylactic effects may be achieved by administration of preventative doses, ranging from 0.01 ug to 100 g per kg of body weight, once or more daily, to once every 20 years. In like fashion, an individual may be made less susceptible to an inflammatory condition that is expected to occur as a result of some medical treatment, e.g., graft versus host disease resulting from the transplantation of cells, tissue or an organ into the individual.

Prophylactic modalities for high risk individuals are also encompassed by the invention. As used herein, the term "high risk individual" is meant to refer to an individual for whom it has been determined, via, e.g., individual or family history or genetic testing, that there is a significantly higher than normal probability of being susceptible to the onset or recurrence of a disease or disorder. For example, a subject animal could have a personal and/or family medical history that includes frequent occurrences of a particular disease or disorder.

As another example, a subject animal could have had such a susceptibility determined by genetic screening according to techniques known in the art (see, e.g., U.S. Congress, Office of Technology Assessment, Chapter 5 In: *Genetic Monitoring and Screening in the Workplace*, OTA-BA-455, U.S. Government Printing Office, Washington, D.C., 1990, pages 75-99). As part of a treatment regimen for a high risk individual, the individual can be prophylactically treated to prevent the onset or recurrence of the disease or disorder. The term "prophylactically effective amount" is meant to refer to an amount of a pharmaceutical composition which produces an effect observed as the prevention of the onset or recurrence of a disease or disorder. Prophylactically effective amounts of a pharmaceutical composition are typically determined by the effect they have compared to the effect observed when a second pharmaceutical composition lacking the active agent is administered to a similarly situated individual.

From in vivo animal studies wherein oligonucleotides have been administered topically or intradermally it has been shown that oligonucleotides become widely distrubuted from the site of administration. For example oligonucleotide ISIS-2302 was topically applied on the back of mini pigs and rats. Samples of dermal and epidermal tissue analyzed by capillary gel electrophoresis and immunohistochemical staining detected significant levels of the oligonucleotide not only at the administration site (back) but also on stomach, neck and hind leg. Accordingly there is provided a method for delivering an oligonucleotide to a first dermal or epidermal tissue site in an animal comprising applying said oligonucleotide to a second dermal or epidermal tissue site in said animal wherein said first site is removed from said second site. In preferred embodiments, the oligonucleotide is administered topically in a pharmaceutical composition of the invention, in particular in an emulsion as described herein. The method is particularly useful for ensuring delivery of oligonucleotide evenly to dermal or epidermal tissue and/or over a great area or to sites that would otherwise be difficult to apply or would be sensitive-to direct administration.

EXAMPLES

The following examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

Example 1

Oligonucleotides

A. General Synthetic Techniques: Oligonucleotides were synthesized on an automated DNA synthesizer using standard phosphoramidite chemistry with oxidation using iodine. Beta-cyanoethyldiisopropyl phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one-1,1-dioxide in acetonitrile for the stepwise thiation of the phosphite linkages.

B. Oligonucleotide Purification: After cleavage from the controlled pore glass (CPG) column (Applied Biosystems) and deblocking in concentrated ammonium hydroxide, at 55° C. for 18 hours, the oligonucleotides were purified by precipitation 2× from 0.5 M NaCl with 2.5 volumes of ethanol followed by further purification by reverse phase high liquid pressure chromatography (HPLC). Analytical gel electrophoresis was accomplished in 20% acrylamide, 8 M urea and 45 mM Tris-borate buffer (pH 7).

C. Oligonucleotide Labeling: In order to follow the distribution of oligonucleotides in situ were radiolabelled to high specific activity by synthetic incorporation of 35S using hydrogen phosphonate chemistry essentially as described by Stein et al. (*Anal. Biochem.*, 1990, 188, 11).

D. Oligonucleotide Structure: The oligonucleotides used in the studies described herein have the following structures and biological activities.

ISIS 2302 is a 2'-deoxyoligonucleotide having a phosphorothioate backbone and the sequence 5'-GCC-CAA-GCT-GGC-ATC-CGT-CA-3' (SEQ ID NO:1). ISIS 2302 is targeted to the 3'-untranslated region (3'-UTR) of the human ICAM-1 gene. ISIS 2302 is described in U.S. Pat. Nos. 5,514,788 and 5,591,623, hereby incorporated by reference.

ISIS 1939 is a 2'-deoxyoligonucleotide having a phosphorothioate backbone and the sequence 5'-CCC-CCA-CCA-CTT-CCC-CTC-TC-3' (SEQ ID NO:2). ISIS 1939 is targeted to the 3'-untranslated region (3'-UTR) of the human ICAM-1 gene. ISIS 1939 is described in U.S. Pat. Nos. 5,514,788 and 5,591,623, hereby incorporated by reference.

ISIS 15839 is a phosphorothioate isosequence "hemimer" derivative of ISIS 2302 having the structure 5'-GCC-CAA-GCT-GGC-ATC-CGT-CA-3' (SEQ ID NO:1), wherein emboldened "C" residues have 5-methylcytosine (m5c) bases and wherein the emboldened, double-underlined residues further comprise a 2'-methoxyethoxy modification (other residues are 2'-deoxy). ISIS 15839 is described in copending U.S. patent application Ser. No. 09/062,416, filed Apr. 17, 1998, hereby incorporated by reference.

ISIS 3082 is a 2'-deoxyoligonucleotide having a phosphorothioate backbone and the sequence 5'-TGC-ATC-CCC-CAG-GCC-ACC-AT-3' (SEQ ID NO:3). ISIS 3082 is targeted to the 3'-untranslated region (3'-UTR) of the murine ICAM-1 gene. ISIS 3082 is described in Stepkowski et al. (*J. Immunol.*, 1994, 153, 5336).

ISIS 2503 is a 2'-deoxyoligonucleotide having a phosphorothioate backbone and the sequence 5'-TCC-GTC-ATC-GCT-CCT-CAG-GG-3' (SEQ ID NO:4). ISIS 2503 is targeted to the translation initiation codon of the human oncogene, Ha-ras. ISIS 2503 is described in U.S. Pat. No. 5,576,208, hereby incorporated by reference.

ISIS 1939 (SEQ ID NO: 2), a phosphorothioate oligonucleotide targeted to a sequence in the 3-untranslated region of ICAM-1 mRNA has been found to exhibit significant biological activity. ISIS 2302 (SEQ ID NO: 1), which hybridizes to the ICAM-1 mRNA at a position 143 bases 3' to the ISIS 1939 target site was also found to be of similar activity in biological assays. Examination of the predicted RNA secondary structure of the human ICAM-1 mRNA 3'-untranslated region (Zuker, *Science*, 1989, 244, 48) surprisingly suggested that both ISIS 1939 and ISIS 2302 hybridize to sequences predicted to be in a stable stem-loop structure of the mRNA. Current dogma suggests that when designing antisense oligonucleotides regions of RNA secondary structure should be avoided. Thus, ISIS 1939 and ISIS 2302 would not have been predicted to inhibit ICAM-1 expression.

ISIS 2302 has been found to inhibit ICAM-1 expression in human umbilical vein cells, human lung carcinoma cells (A549), human epidermal carcinoma cells (A431), and human keratinocytes. ISIS 2302 has also demonstrated specificity for its target ICAM-1 over other potential nucleic acid targets such as HLA-α and HLA-β. Both ISIS 2302 (SEQ ID NO:1) and ISIS 1939 (SEQ ID NO:2) markedly reduced ICAM-1 expression, as detected by northern blot analysis to determine mRNA levels, in C8161 human melanoma cells. In an experimental metastasis assay, ISIS 2302 decreased the metastatic potential of C8161 cells, and eliminated the enhanced metastatic ability of C8161 cells resulting from TNF-α treatment. ISIS 2302 has also shown significant biological activity in animal models of inflammatory disease. The data from animal testing has revealed strong anti-inflammatory effects of ISIS 2302 in a number of inflammatory diseases including Crohn's disease, rheumatoid arthritis, psoriasis, ulcerative colitis, and kidney transplant rejection. When tested on humans, ISIS 2302 has shown good safety and activity against Crohn's disease. Further ISIS 2302 has demonstrated a statistically significant steroid-sparing effect on treated subjects such that even after five months post-treatment subjects have remained weaned from steroids and in disease remission. This is a surprising and significant finding regarding ISIS 2302's therapeutic effects.

Example 2

Sources of Compounds

In general, the compounds used in the studies described herein are available from a variety of commercial sources, or can be synthesized from available reagents by those skilled in the art using methods known in the art. For sake of convenience, some specific commercial suppliers of the more significant compounds used in, or identified by, the studies described herein are provided in the following list.

Chol (cholesterol) is purchased from Avanti Polar Lipids, Inc. (Alabaster, Ala.) or from Sigma Chemical Corp. (St. Louis, Mo.).

1-Dodecyl-2-pyrrolidinone is purchased from Aldrich Chemical Co. (Milwaukee, Wis.).

DOPE (dioleoylphosphatidylethanolamine) is purchased from Avanti.

DMPC (dimyristoylphosphatidylcholine) is purchased from Avanti or Sigma.

DPPC (dipalmitoylphosphatidylcholine) is purchased from Sigma, Avanti or Genzyme Corp. (Cambridge, Mass.).

DMPG (dimyristoylphosphatidylglycol) is purchased from Avanti or Sigma.

DMSO (dimethyl sulfoxide) is purchased from Sigma or Aldrich.

IPM (isopropyl myristate, a.k.a. myristic acid isopropyl ester) is purchased from Sigma or Aldrich.

Menthone is purchased from Aldrich.

1-Methyl-2-pyrrolidinone is purchased from Sigma.

Oleic acid is purchased from Sigma.

PG (propylene glycol, a.k.a. 1,2-propanediol) is purchased from Sigma or Aldrich.

Tween 40 [polyoxyethylene(2)sorbitan monopalmitate] is purchased from Sigma or Aldrich.

Azone (dodecyl azone, a.k.a. laurocapram) is purchased from Shanghai Daniel Chem Technologies Co., Ltd., Shanghai, People's Republic of China.

Limonene (d-limonene) is purchased from Sigma.

MIGLYOL™ 818 is purchased from Hhls AG, Marl, Germany.

Example 3

In Vitro Skin Testing

Male and female hairless SKH1 mice 6-8 weeks old were obtained from Charles River Laboratories (Wilmington, Mass.) and were euthanized using carbon dioxide asphyxiation. Fresh and frozen skins were mounted on a vertical Franz diffusion cell (Permegear, N.J.) with each skin having a diffusional area of 0.636 $cm^2$. Receptor chambers having a volume of 5.1 ml were filled with isotonic phosphate buffer (pH 7.2) containing 0.1% (v/v) of 36% aqueous formaldehyde as preservative. Receptor temperatures were maintained at 37±0.5° C. and stirred continuously at 600 rpm. The skins were allowed to hydrate for 1 hour prior to starting an experiment. Experiments generally were performed at 24 hours.

Penetration enhancers/vehicles were added into the donor compartment for 1 hour and then washed off with 500 µl of methanol. The total amount of enhancer/vehicle that was added to each donor compartment was 10 µl (unless otherwise noted). After methanol wash, the skin was lightly wiped and blown dry to remove any visible moisture. In an experiment studying the effect of methanol on penetration enhancement, no wash was performed. Also, in experiments studying the effects of pretreatment time, the amount of time the enhancer was allowed to stay on the skin was varied (i.e., minutes or 1, 2 or 3 hours).

Olignucloetide [i.e., ISIS 2302 (SEQ ID NO:1)] was added on top of the enhancer solution. ISIS 2302 was added to each donor compartment as a 200 µl normal saline solution containing both 1 mg of unlabeled oligonucleotide radiolabeled oligonucleotide and approximately 300,000 decays per minute ("DPM") of radiolabeled oligonucleotide. Epidermal, dermal and receptor penetration values are expressed as the ratio of the counts penetrated versus the control counts.

The following chemicals were used as enhancers/vehicles: propylene glycol (PG), dimethyl sulfoxide (DMSO), isopropyl myristate (IPM), Azone, MIGLYOL™ 818, oleic acid, d-limonene, limonene, 1-dodecyl-2-pyrrolidinone (1dodecyl2pyrrol), 1-methyl-2-pyrrolidinone (1Methyl2pyrrol), menthone, ethanol and TWEEN 40.

Statisical analyses were performed on Excel using Studentsʼ t-test (two-sample assuming equal variances) along with averages, standard deviations, and standard errors. Female hairless mice were preferentially used as the studies progressed due to an uncharacterized but recurring follicular infection that appeared to preferentially target male mice.

As shown in FIG. 1, the best epidermal penetration enhancers for the delivery of ISIS 2302 are isopropyl myristate ("IPM"; 1.67%, 2.14% and 3.11%), menthone (2.93%), ethylene glycol (2.41%), 1-methyl-2-pyrrolidinone ("1Methyl2pyrrol"; 2.41%), d-limonene (1.55%), MIGLYOL 818® (1.62%) and dimethyl sulfoxide (DMSO; 1.56%). In contrast, for dermal penetration, the best penetration enhancers are Tween 40 (1.42%), oleic acid (~1.0%), d-limonene (0.72%), 1-dodecyl-2-pyrrolidinone ("1dodecyl2pyrrol"; 0.67%), DMSO (0.38%) and 1-methyl-2-pyrrolidinone ("1Methyl2pyrrol"; 0.25%). There is no little or no correlation between epidermal penetration enhancement and dermal penetration enhancement, an effect which may be due to different mechanisms of action of delivery to the two layers, rates of penetration, the duration of the experiments, the duration of enhancer pretreatments, or a combination of such factors.

"Receptor penetration" in the tables refers to the percentage dose that migrates through the isolated skin and thus deposits in a receptacle at the end of the experimental set-up. A high value in this column indicates the formulation has potential as a systemic delivery vehicle.

Experiments with Azone were carried out to examine how much of a factor methanol is in the delivery of Isis 2302; these results are also shown in FIG. 1. Azone pretreatment with a methanol wash resulted in epidermal and dermal penetration values of 1.31% and 0.16%, respectively, whereas the values for experiments without methanol values were 0.72% and 0.13% for epidermal and dermal penetration, respectively. Ethanol had little effect on the penetration of ISIS 2302 when limonene was used as an enhancer. Higher volumes of limonene and isopropyl myristate did not result in an increase in the penetration.

Example 4

Cream Formulations and Effects of Oligonucleotide Chemistries

Studies were carried out to optimize the formulation containing isopropyl myristate, and the results are shown in FIG. 2. Duration of pretreatment ranging from 30 minutes to 3 hours had little effect on the penetration of ISIS 2302. Lower concentration of isopropyl myristate in the range of 10 to 35% v/v in water reduced the penetration significantly; however, the coarse mixture of isopropyl myristate and water applied in very small quantities (10-30 µL) may have resulted in spotty coverage of the skin. Lower amounts of ISIS 2302 resulted in an increase in the percent of applied dose penetrated.

In order to formulate a cream from isopropyl myristate, its viscosity was increased using oil soluble agents and surfactants such as glyceryl monosterate, stearic acid and bees wax. Oligonucleotide was dissolved in a water phase consisting of aqueous surfactants and viscosity imparting agents such as polyoxyl-40 stearate and polyethylene glycol derivatives. Cream formulations consisting of Water (36-45% w/w), Isopropyl Myristate (30-48% w/w), Glyceryl monostearate (10-16% w/w), Polyoxyl-40 Stearate (0-15% w/w) and antimicrobial preservatives (benzyl alcohol, methylparaben, propylparaben) were studied in vitro for penetration. Oligonucleotide was thoroughly mixed with the cream formulations to give a final concentration of 1 mg oligonucleotide for each 149 mg cream. Appropriate controls were used to determine the radioactivity per mg of cream.

The cream formulation with 30% isopropyl myristate resulted in an epidermal penetration of 1.66% and a dermal penetration of 1.57% for ISIS 2302 (FIG. 2). Similar penetration values were seen with cream formulation containing 48% isopropyl myristate.

A cream formulation of ISIS 15839, a 5-methylcytosine-comprising 2'-methoxyethoxy isosequence hemimer derivative of ISIS 2302, with 30% isopropyl myristate showed a very high dermal penetration, i.e., 11% of the applied dose. The results presented in FIG. 2 thus demonstrate that oligonucleotides of different chemical compositions penetrate the skin when formulated in isopropyl myristate cream formulations.

Example 5

In Vivo Testing of ICAN-1 Suppression

The oligonucleotide ISIS 3082 (SEQ ID NO:3), which is targeted to the murine ICAM-1 gene, was mixed with empty ("f") liposomes or encapsulated into ("e") liposomes as set forth below to determine the degree of ICAM-1 suppression effected thereby:
1. DOPE-f Liposomes (DOPE:DPPC:Chol; 20:60:20% w/w) mixed with ISIS 3082 to obtain 10 mg/mL ISIS 3082;
2. ISIS 3082 solution at 10 mg/mL;
3. DOPE-f Liposomes (DOPE:DPPC:Chol; 20:60:20% w/w) mixed with ISIS 3082 to obtain 10 mg/mL ISIS 3082;
4. DOPE-e Liposomes (DOPE:DPPC:Chol; 20:60:20% w/w) with ISIS 3082 encapsulated in the liposomes, not purified, to obtain 10 mg/mL ISIS 3082;
5. DMPG-f Liposomes (DMPG:DPPC:Chol; 20:60:20% w/w) mixed with ISIS 3082 to obtain 10 mg/mL ISIS 3082;
6. DMPG-e Liposomes (DMPG:DPPC:Chol; 20:60:20% w/w) with ISIS 3082 encapsulated in the liposomes, not purified, to obtain 10 mg/mL-ISIS 3082;
7. DMPC-f Liposomes (DMPC:DPPC:Chol; 20:60:20% w/w) mixed with ISIS 3082 to obtain 10 mg/mL ISIS 3082;
8. DMPC-e Liposomes (DMPC:DPPC:Chol; 20:60:20% w/w) with ISIS 3082 encapsulated in the DMPC liposomes, not purified, to obtain 10 mg/mL ISIS 3082;
12. No treatment, phorbol myristate acetate ("PMA") positive control; and
13. No treatment, no PMA control ("basal").

Liposome Preparation: The liposomes were prepared by hydrating a dry film of lipids in a glass container with either phosphate buffered saline at pH 7.4 or a 10 mg/mL solution of ISIS 3082 in PBS. The hydrated lipids were then extruded 21 times through a 50 nm membrane to form small liposomes with final lipid concentration of ~100 mg/mL, drug concentration of ~10 mg/mL and particle size of ~100 nm.

Animal Studies: Liposome formulations were applied to the back of hairless mice using a Hilltop™ chamber (Hilltop Research, Cincinnati, Ohio) that keeps the formulation in place. Three mice were tested in each group. Forty-eight hours after the formulation application, the treated part of the skin was challenged with PMA to induce ICAM-1. Mice were sacrificed 4 hours after PMA application and skin collected for Northern analyses of the mRNA levels, which were performed essentially according to the protocol detailed in Examples 3 and 7 of co-pending U.S. patent application Ser. No. 09/062,416, filed Apr. 17, 1998, hereby incorporated by reference.

The results with ISIS 3082 mixed with empty liposomes are as follows:

| Formulation | Relative mRNA Level (PMA = 100%) |
| --- | --- |
| Basal | 12.46 ± 2.39 |
| DOPE-f (#1) | 71.80 ± 7.93 |
| DOPE-f (#2) | 64.02 ± 11.32 |
| DMPG-f | 63.84 ± 11.54 |
| DPPC-f | 91.80 ± 0.25 |
| PBS | 93.91 ± 11.04 |

The DOPE and DMPG liposomes show about 30% to about 40% reduction in PMA-induced ICAM-1 expression, whereas the phosphate buffered saline solution formulation and DPPC liposomes show much lower reduction. The results prove that ISIS 3082 penetrates the skin when mixed with liposomes and that the penetration of drug thus achieved is sufficient to cause a biological effect.

The results with ISIS 3082 encapsulated in the liposomes are as follows:

| Formulation | Relative mRNA Level (PMA = 100%) |
| --- | --- |
| Basal | 12.46 ± 2.39 |
| DOPE-e | 69.95 ± 5.19 |
| DPPC-e | 67.19 ± 11.99 |
| DMPG-e | 58.54 ± 12.40 |

The liposome formulations comprising DOPE, DPPC or DMPG and encapsulating ISIS 3082 all show a 30-50% reduction in ICAM-1 mRNA, showing that ISIS 3082 penetrates the skin when encapsulated in liposomes and that the penetration of drug thus achieved is sufficient to cause a biological effect.

Example 6

Comparison of Topical and Systemic Administration of Oligonucleotides

In order to develop a formulation for the local delivery of oligonucleotides via topical administration, the following experiments were carried out.

Formulations: A cream formulation of 2% ISIS 2503 (SEQ ID NO:4), intended for topical application, was compared to 20 mg/mL formulations in saline administered via intravenous, subcutaneous or intradermal means.

The cream formulation was prepared by heating the oil phase [containing isopropyl myristate (30% w/w) and glyceryl monostearate (10% w/w)] and the aqueous phase [containing water (45% w/w) and polyoxyl-40-stearate (15% w/w)] to 70° C. followed by homogenization at 7,000 rpm using a Silverson L4RT mixer (Silverson Machines, East Long Meadows, Mass.), after which the mixture was allowed to cool to room temperature. The particle size of the oil phase droplet in the cream had a mean diameter of 1.0 um. ISIS 2503 was mixed with the cream by trituration.

Animal Studies: SCID mice (Taconic Farms, Inc., Germantown, N.Y.) ~6 weeks old, were transplanted with human skin and allowed to establish the xenograft for 6 weeks. 200 mg cream or 20 mg/kg solution were administered at 48, 24 and 4 hours prior to TNF-a administration. TNF-α was injected in to the xenograft to induce inflammation. Mice were sacrificed and skin isolated for immunohistochemistry.

Stained tissue samples show a pronounced accumulation of the oligonucleotides in the nuclei of the cells in the viable epidermis upon treatment with the cream formulations. Accumulation is also seen in the dermis but no nuclear accumulation is visible. The cream formulation thus provides for the selective delivery of oligonucleotides to cells of the dermis.

In contrast, photomicrographs of skin treated intravenously with the solution formulation show accumulation of oligonucleotide in the dermis but no nuclear accumulation is visible. There was no accumulation in the epidermis.

Similarly, photomicrographs of skin treated intradermally with the solution formulation show a large amount of oligonucleotide in the proximity of the needle tract in the dermis and some in the epidermis. Again, however, there is no nuclear accumulation.

Taken together, the preceding results show that oligonucleotide delivered to the dermis by systemic or direct injection route does not accumulate in the cells of viable epidermis whereas topical delivery with the cream formulation can target the viable epidermis. The cream formulation can thus be used to prepare pharmaceutical and other formulations comprising any of a variety of oligonucleotides, including but not limited to those described herein, intended for dermal delivery. The invention thus provides methods for preventing or treating a variety of dermal disease and disorders, such methods comprising contacting the skin of an animal with a pharmaceutical composition comprising an oligonucleotide according to the present disclosure.

Example 7

IPM Cream Formulations

An oil phase was prepared by dissolving methylparaben (3 mg), propylparaben (4.8 mg), phenoxyethanol (10 mg) and glycerol monostearate (100 mg) in heated isopropyl myristate IPM (100 mg). The aqueous phase was prepared by dissolving monobasic sodium phosphate monohydrate (3 mg) and dibasic sodium phosphate heptahydrate (9 mg) in a target weight of water for a 1 g total formulation. The pH of the aqueous solution was adjusted to 7±0.2 with 1N monobasic sodium phosphate and 1N sodium hydroxide. The solution was heated and methylparaben (2 mg), propylparaben (0.2 mg), phenoxyethanol (15 mg) and polyoxyl 40 stearate (150 mg) were then added followed by hydroxypropyl methylcellulose (5 mg) and oligonucleotide ISIS-2302 (0.1 mg, 1 mg, 5 mg and 20 mg). The oil phase was then added to the water phase while homogenizing to form the emulsion which was then cooled to room temperature.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

It is intended that each of the patents, applications, printed publications, and other published documents mentioned or referred to in this specification be herein incorporated by reference in their entirety.

What is claimed is:

1. A pharmaceutical composition comprising an oligonucleotide admixed with a topical delivery agent comprising a penetration enhancing amount of isopropyl myristate, wherein said composition is formulated into a cream or emulsion, with the proviso that said oligonucleotide is not an oligonucleotide that is complementary to a portion of a mRNA sequence coding for tumor necrosis factor and inhibits the expression of the tumor necrosis factor.

2. The composition of claim 1, wherein said composition comprises 10% to 50% isopropyl myristate.

3. The composition of claim 1, wherein said composition comprises about 30%-48% isopropyl myristate.

4. The composition of claim 1, wherein said composition further comprises 10%-16% glyceryl monostearate.

5. The composition of claim 1, wherein said composition further comprises glyceryl monooleate.

6. The composition of claim 1, wherein said composition further comprises up to 15% polyoxl-40-stearate.

7. The composition of claim 1, wherein said composition further comprises polyoxylethylene-20-cetyl ether.

8. The composition of claim 1, wherein said composition further comprises glyceryl monostearate.

9. The composition of claim 1, wherein said composition further comprises 5% to 20% glyceryl monostearate.

10. The composition of claim 1, wherein said composition comprises about 2% of said oligonucleotide.

11. The composition of claim 1, wherein said composition is formulated into a cream.

12. The composition of claim 1, wherein said composition is formulated into an emulsion.

13. The composition of claim 1, wherein said oligonucleotide comprises at least one modified internucleoside linkage, at lease one nucleoside comprising a modified sugar, or at least one nucleobase comprises a modified nucleobase.

14. The composition of claim 13, wherein each internucleoside linkage is a phosphorothioate internucleoside linkage.

15. The composition of claim 13, wherein at least one modified sugar comprises a 2'-O-methoxyethyl.

16. The composition of claim 13, wherein the modified nucleobase is a 5-methylcytosine.

17. The composition of claim 1, wherein the oligonucleotide is about 8 to about 100 nucleotides in length.

18. The composition of claim 1, wherein the oligonucleotide is about 10 to about 30 nucleotides in length.

19. The composition of claim 1, wherein the oligonucleotide consists of 20 linked nucleosides.

20. The composition of claim 1, wherein the oligonucleotide is a single-stranded oligonucleotide.

21. The composition of claim 1, wherein said oligonucleotide is a gapmer.

22. The composition of claim 1, wherein said oligonucleotide is about 10 to 30 nucleotides in length, wherein said oligonucleotide is a gapmer having a central deoxynucleotide region flanked on each of the 5' and 3' ends of said deoxynucleotide region with a wing region comprising at least one 2'-O-methoxyethyl substituted nucleoside, wherein each internucleoside linkage in said oligonucleotide is a phosphorothioate linkage, and wherein each cytosine in said oligonucleotide is a 5-methylcytosine.

23. The composition of claim 1, wherein the oligonucleotide is a pharmaceutically acceptable salt.

24. A pharmaceutical composition for topical delivery of an antisense oligonucleotide, comprising:
  an antisense oligonucleotide;
  a penetration enhancing amount of isopropyl myristate; and
  10%-16% glyceryl monosterate, wherein said composition is formulated into a cream or emulsion,
  with the proviso that said antisense oligonucleotide is not an oligonucleotide that is complementary to a portion of a mRNA sequence coding fox tumor necrosis factor and inhibits the expression of the tumor necrosis factor.

25. The composition of claim 24, wherein said composition comprises 10% to 50% isopropyl myristate.

26. The composition of claim 24, wherein said composition comprises about 30%-48% isopropyl myristate.

27. The composition of claim 24, wherein said composition further comprises up to 15% polyoxl-40-stearate.

28. The composition of claim 24, wherein said composition comprises about 2% of said antisense oligonucleotide.

29. The composition of claim 24, wherein said composition is formulated into a cream.

30. The composition of claim 24, wherein said composition is formulated into an emulsion.

31. The composition of claim 24, wherein said antisense oligonucleotide comprises at least one modified internucleoside linkage, at lease one nucleoside comprising a modified sugar, or at least one nucleobase comprising a modified nucleobase.

32. The composition of claim 31, wherein each internucleoside linkage is a phosphorothioate internucleoside linkage.

33. The composition of claim 31, wherein at least one modified sugar comprises a 2'-O-methoxyethyl.

34. The composition of claim 31, wherein the modified nucleobase is a 5-methylcytosine.

35. The composition of claim 24, wherein the antisense oligonucleotide is about 8 to about 100 nucleotides in length.

36. The composition of claim 24, wherein the antisense oligonucleotide is about 10 to about 30 nucleotides in length.

37. The composition of claim 24, wherein the antisense oligonucleotide consists of 20 linked nucleosides.

38. The composition of claim 24, wherein the antisense oligonucleotide is a single-stranded oligonucleotide.

39. The composition of claim 24, wherein said antisense oligonucleotide is a gapmer.

40. The composition of claim 24, wherein said antisense oligonucleotide is about 10 to 30 nucleotides in length, wherein said antisense oligonucleotide is a gapmer having a central deoxynucleotides region flanked on each of the 5' and 3' ends of said deoxynucleotides region with a wing region comprising at least one 2'-O-methoxyethyl substituted nucleoside, wherein each internucleoside linkage in said antisense oligonucleotide is a phosphorothioate linkage, and wherein each cytosine in said antisense oligonucleotide is a 5-methylcytosine.

41. The composition of claim 24, wherein the antisense oligonucleotide is a pharmaceutically acceptable salt.

42. The composition of claim 22, wherein said composition comprises 10% to 50% isopropyl myristate.

43. The composition of claim 40, wherein said composition comprises 10% to 50% isopropyl myristate.

* * * * *